(12) United States Patent
Terzibashian

(10) Patent No.: US 9,744,333 B2
(45) Date of Patent: Aug. 29, 2017

(54) PACKAGING FOR CATHETER TREATMENT DEVICES AND ASSOCIATED DEVICES, SYSTEMS AND METHODS

(71) Applicant: Medtronic Ardian Luxembourg S.a.r.l., Luxembourg (LU)

(72) Inventor: Hagop Terzibashian, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 0 days.

(21) Appl. No.: 14/655,450

(22) PCT Filed: Oct. 18, 2013

(86) PCT No.: PCT/US2013/065791
§ 371 (c)(1),
(2) Date: Jun. 25, 2015

(87) PCT Pub. No.: WO2014/063119
PCT Pub. Date: Apr. 24, 2014

(65) Prior Publication Data
US 2015/0352316 A1     Dec. 10, 2015

Related U.S. Application Data

(63) Continuation-in-part of application No. 13/840,484, filed on Mar. 15, 2013, now abandoned.
(Continued)

(51) Int. Cl.
*B65D 83/10* (2006.01)
*A61M 25/00* (2006.01)
(Continued)

(52) U.S. Cl.
CPC ............ *A61M 25/002* (2013.01); *B65D 1/34* (2013.01); *B65D 25/108* (2013.01); *B65D 43/16* (2013.01)

(58) Field of Classification Search
CPC ............ A61M 25/002; A61M 25/0021; A61M 25/0023; A61M 25/0024; A61M 25/0025;
(Continued)

(56) References Cited

U.S. PATENT DOCUMENTS

| 4,216,860 A | 8/1980 | Heimann |
| 4,602,624 A | 7/1986 | Naples et al. |

(Continued)

FOREIGN PATENT DOCUMENTS

| WO | WO9407446 | 4/1994 |
| WO | WO-9525472 | 9/1995 |

(Continued)

OTHER PUBLICATIONS

European Search Report for European Application No. 13159256, Date Mailed: Oct. 17, 2013, 6 pages.
(Continued)

*Primary Examiner* — Steven A. Reynolds
*Assistant Examiner* — Javier A Pagan

(57) ABSTRACT

Packaging (5) for catheter treatment devices, such as catheters (10) including multi-electrode arrays (6), are disclosed herein. In one embodiment, for example, a catheter package assembly comprises a tray (50), a lid (80), and a coiled sheath (30) disposed in the tray. The tray includes at least one pocket (54) adapted to receive a distal end portion of a catheter. The tray and lid each include cooperative latching features (90). The sheath defines a lumen that is configured to receive an elongate shaft (4) of the catheter.

10 Claims, 24 Drawing Sheets

Related U.S. Application Data

(60) Provisional application No. 61/716,451, filed on Oct. 19, 2012.

(51) Int. Cl.
*B65D 43/16* (2006.01)
*B65D 1/34* (2006.01)
*B65D 25/10* (2006.01)

(58) Field of Classification Search
CPC .......... A61M 25/0026; A61M 25/0028; A61M 25/0029; A61M 25/003; B65D 1/34; B65D 1/36; B65D 25/10; B65D 25/101; B65D 25/103; B65D 25/105; B65D 25/106; B65D 25/107; B65D 25/108; B65D 43/14; B65D 43/16; B65D 43/161; B65D 43/162
USPC ....... 206/438, 363, 364, 365, 461, 462, 436, 206/467, 470, 471, 485; 220/4.21, 4.22, 220/4.23, 4.24, 6
See application file for complete search history.

(56) References Cited

U.S. PATENT DOCUMENTS

| | | |
|---|---|---|
| 4,649,936 A | 3/1987 | Ungar et al. |
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,683,345 A | 11/1997 | Waksman et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,846,196 A | 12/1998 | Siekmeyer et al. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,947,284 A * | 9/1999 | Foster .................... A61B 50/33 206/364 |
| 5,954,719 A | 9/1999 | Chen et al. |
| 5,972,008 A * | 10/1999 | Kalinski ................. A61B 50/33 206/440 |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,533,116 B1 | 3/2003 | Riley |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,917,834 B2 | 7/2005 | Koblish et al. |
| 6,923,808 B2 | 8/2005 | Taimisto |
| 6,939,346 B2 | 9/2005 | Kannenberg et al. |
| 6,949,097 B2 | 9/2005 | Stewart et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,234,597 B2 * | 6/2007 | Rowe .................... A61M 25/002 206/364 |
| 7,243,791 B2 * | 7/2007 | Detruit .................. A61F 2/0095 206/363 |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0159966 A1 | 8/2003 | McMichael et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |

(56) References Cited

U.S. PATENT DOCUMENTS

| | | | |
|---|---|---|---|
| 2006/0212076 | A1 | 9/2006 | Demarais et al. |
| 2006/0271111 | A1 | 11/2006 | Demarais et al. |
| 2007/0129720 | A1 | 6/2007 | Demarais et al. |
| 2007/0265687 | A1 | 11/2007 | Deem et al. |
| 2008/0319513 | A1 | 12/2008 | Pu et al. |
| 2009/0036948 | A1 | 2/2009 | Levin et al. |
| 2010/0137860 | A1 | 6/2010 | Demarais et al. |
| 2010/0137952 | A1 | 6/2010 | Demarais et al. |
| 2010/0191112 | A1 | 7/2010 | Demarais et al. |
| 2010/0222851 | A1 | 9/2010 | Deem et al. |
| 2010/0222854 | A1 | 9/2010 | Demarais et al. |
| 2011/0034832 | A1 | 2/2011 | Cioanta et al. |
| 2012/0130289 | A1 | 5/2012 | Demarais et al. |
| 2012/0130345 | A1 | 5/2012 | Levin et al. |
| 2012/0172837 | A1 | 7/2012 | Demarais et al. |
| 2013/0218029 | A1 | 8/2013 | Cholette et al. |

FOREIGN PATENT DOCUMENTS

| | | |
|---|---|---|
| WO | WO-9531142 | 11/1995 |
| WO | WO-9736548 | 10/1997 |
| WO | WO9842403 | 10/1998 |
| WO | WO-99/00060 | 1/1999 |
| WO | WO-0122897 | 4/2001 |
| WO | WO-0170114 | 9/2001 |
| WO | WO03022167 | 3/2003 |
| WO | WO03082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008049084 | 4/2008 |

OTHER PUBLICATIONS

Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.

Avitall et al., "The creation of linear contiguous lesions in the atria with an expandable loop catheter," Journal of the American College of Cardiology, 1999; 33; pp. 972-984.

Beale et al., "Minimally Invasive Treatment for Varicose Veins: A Review of Endovenous Laser Treatment and Radiofrequency Ablation". Lower Extremity Wounds 3(4), 2004, 10 pages.

Blessing, Erwin et al., Cardiac Ablation and Renal Denervation Systems Have Distinct Purposes and Different Technical Requirements, JACC Cardiovascular Interventions, vol. 6, No. 3, 2013, 1 page.

ClinicalTrials.gov, Renal Denervation in Patients with uncontrolled Hypertension in Chinese (2011), 6pages. www.clinicaltrials.gov/ct2/show/NCT01390831.

Excerpt of Operator's Manual of Boston Scientific's EPT-1000 XP Cardiac Ablation Controller & Accessories, Version of Apr. 2003, (6 pages).

Excerpt of Operator's Manual of Boston Scientific's Maestro 30000 Cardiac Ablation System, Version of Oct. 17, 2005 , (4 pages).

Schneider, Peter A., "Endovascular Skills—Guidewire and Catheter Skills for Endovascular Surgery," Second Edition Revised and Expanded, 10 pages, (2003).

Kandarpa, Krishna et al., "Handbook of Interventional Radiologic Procedures", Third Edition, pp. 194-210 (2002).

ThermoCool Irrigated Catheter and Integrated Ablation System, Biosense Webster (2006), 6 pages.

Mount Sinai School of Medicine clinical trial for Impact of Renal Sympathetic Denervation of Chronic Hypertension, Mar. 2013, 11 pages. http://clinicaltrials.gov/ct2/show/NCT01628198.

Opposition to European Patent No. EP2092957, Granted Jan. 5, 2011, Date of Opposition Oct. 5, 2011, 26 pages.

Opposition to European Patent No. EP1802370, Granted Jan. 5, 2011, Date of Opposition Oct. 5, 2011, 20 pages.

Opposition to European Patent No. EP2037840, Granted Dec. 7, 2011, Date of Opposition Sep. 7, 2012, 25 pages.

Oz, Mehmet, Pressure Relief, TIME, Jan. 9, 2012, 2 pages. <www.time.come/time/printout/0,8816,2103278,00.html>.

Prochnau, Dirk et al., Catheter-based renal denervation for drug-resistant hypertension by using a standard electrophysiology catheter; Euro Intervention 2012, vol. 7, pp. 1077-1080.

Purerfellner, Helmut et al., Pulmonary Vein Stenosis Following Catheter Ablation of Atrial Fibrillation, Curr. Opin. Cardio. 20: 484-490, 2005.

Papademetriou, Vasilios, Renal Sympathetic Denervation for the Treatment of Difficult-to-Control or Resistant Hypertension, Int. Journal of Hypertension, 2011, 8 pages.

Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.

Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.

Tsao, Hsuan-Ming, Evaluation of Pulmonary Vein Stenosis after Catheter Ablation of Atrial Fibrillation, Cardiac Electrophysiology Review, 6, 2002, 4 pages.

Wittkampf et al., "Control of radiofrequency lesion size by power regulation," Journal of the American Heart Associate, 1989, 80: pp. 962-968.

Zheng et al., "Comparison of the temperature profile and pathological effect at unipolar, bipolar and phased radiofrequency current configurations," Journal of Interventional Cardiac Electrophysiology, 2001, pp. 401-410.

U.S. Appl. No. 60/852,787, filed Oct. 18, 2006, 105 pages.

Pieper et al., "Design and Implementation of a New Computerized System for Intraoperative Cardiac Mapping." Journal of Applied Physiology, 1991, vol. 71, No. 4, pp. 1529-1539.

Allen, E.V., Sympathectomy for essential hypertension, Circulation, 1952, 6:131-140.

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, The American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

Krum, et al., "Renal Sympathetic-Nerve Ablation for Uncontrolled Hypertension." New England Journal of Med, Aug. 2009, 361; 9, 3 pages.

Luippold, Gerd et al., "Chronic Renal Denervation Prevents Glomerular Hyperfiltration in Diabetic Rats", Nephrol Dial Transplant, vol. 19, No. 2, 2004, pp. 342-347.

(56) References Cited

OTHER PUBLICATIONS

Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012 Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al. "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.

(56) References Cited

OTHER PUBLICATIONS

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*, 174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

(56) References Cited

OTHER PUBLICATIONS

Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
Opposition to European Patent No. 2465470, Granted Oct. 28, 2015, Date of Opposition Jul. 27, 2016, 34 pp.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
U.S. Appl. No. 11/363,867, filed Feb. 27, 2006, 70 pp.
U.S. Appl. No. 60/813,589, filed Dec. 29, 2005, 62 pp.
Ureter, https://en.wikipedia.org/wiki/Ureter, Jun. 2016, 6 pp.

\* cited by examiner

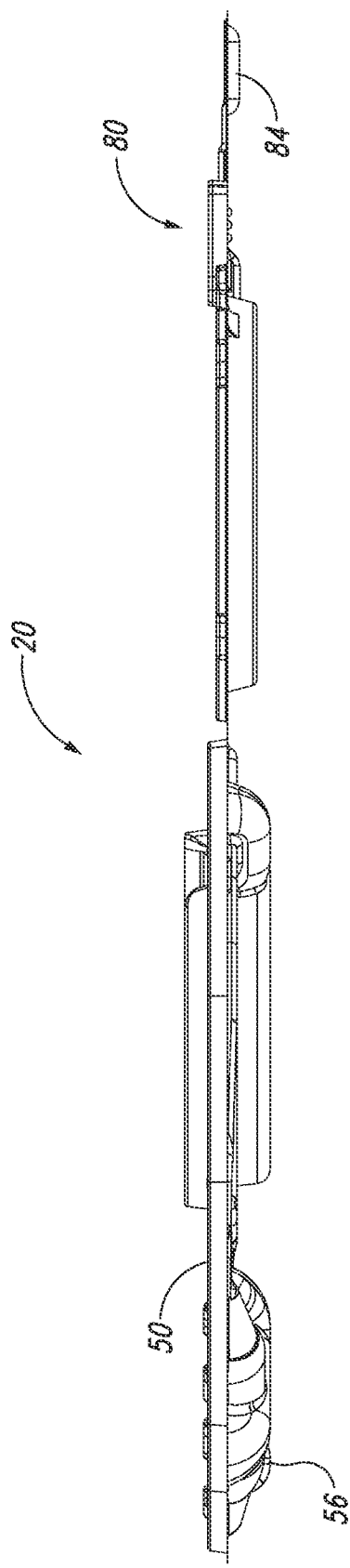
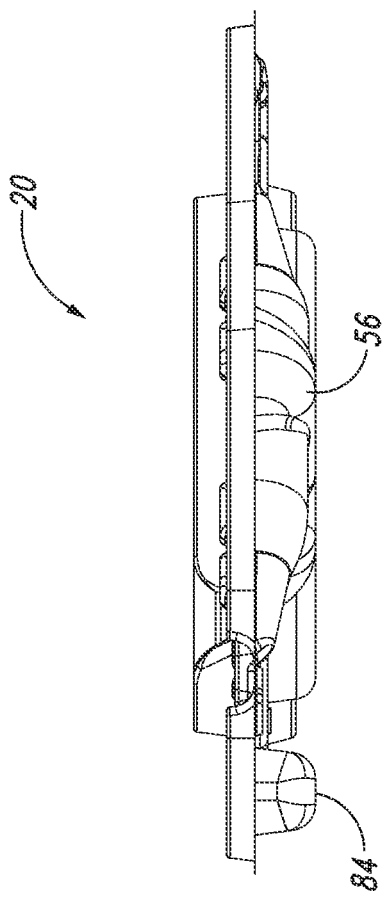

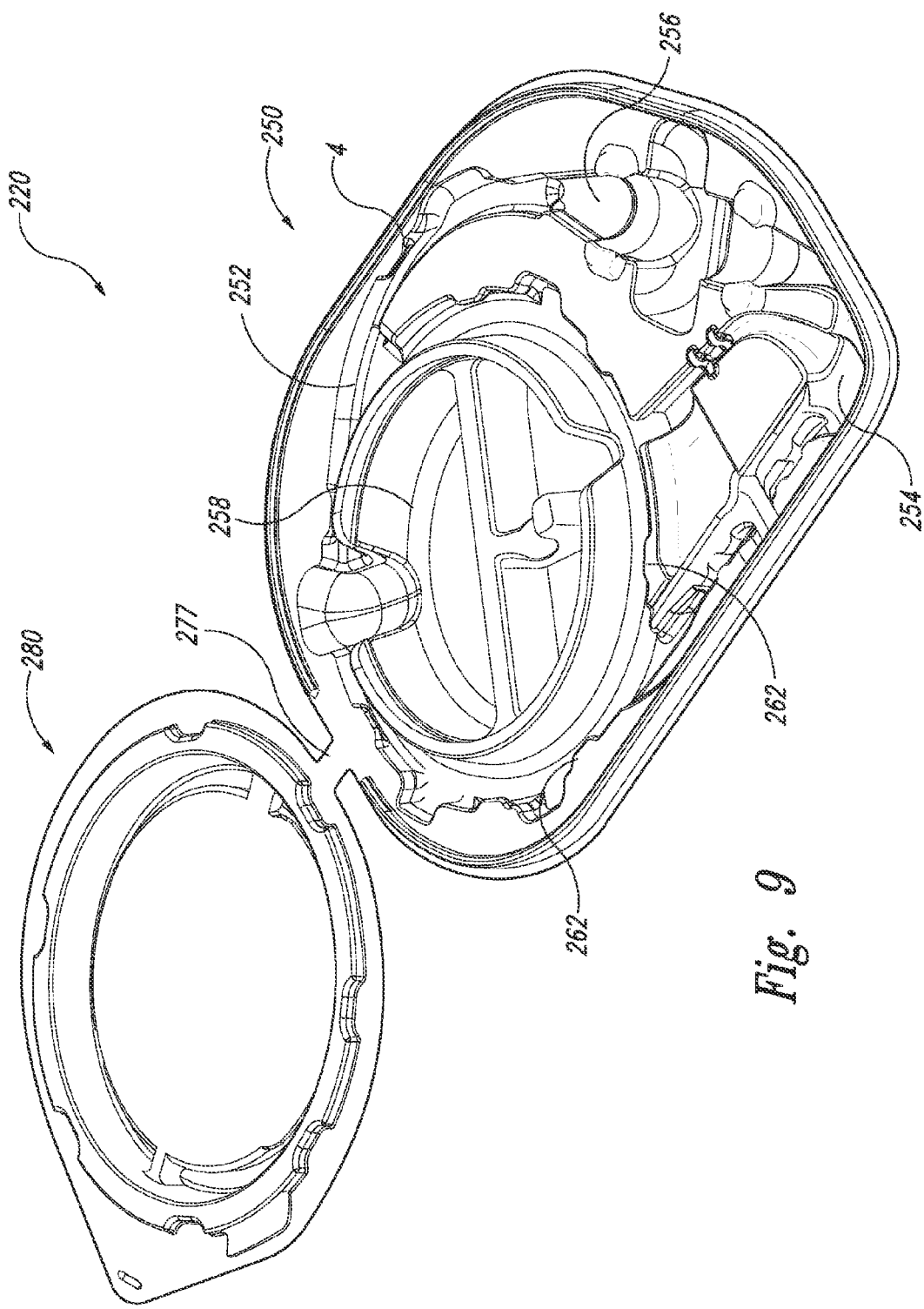

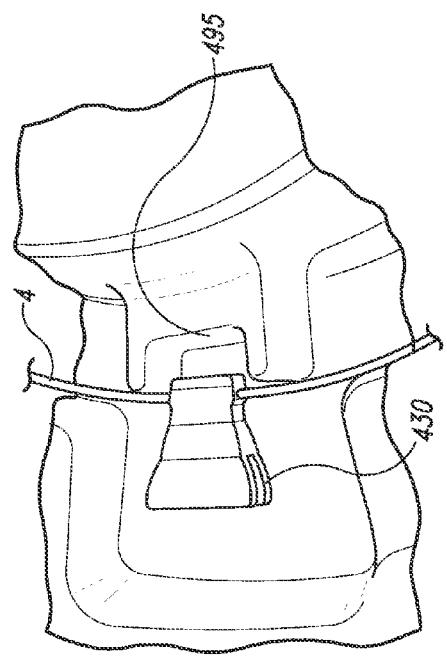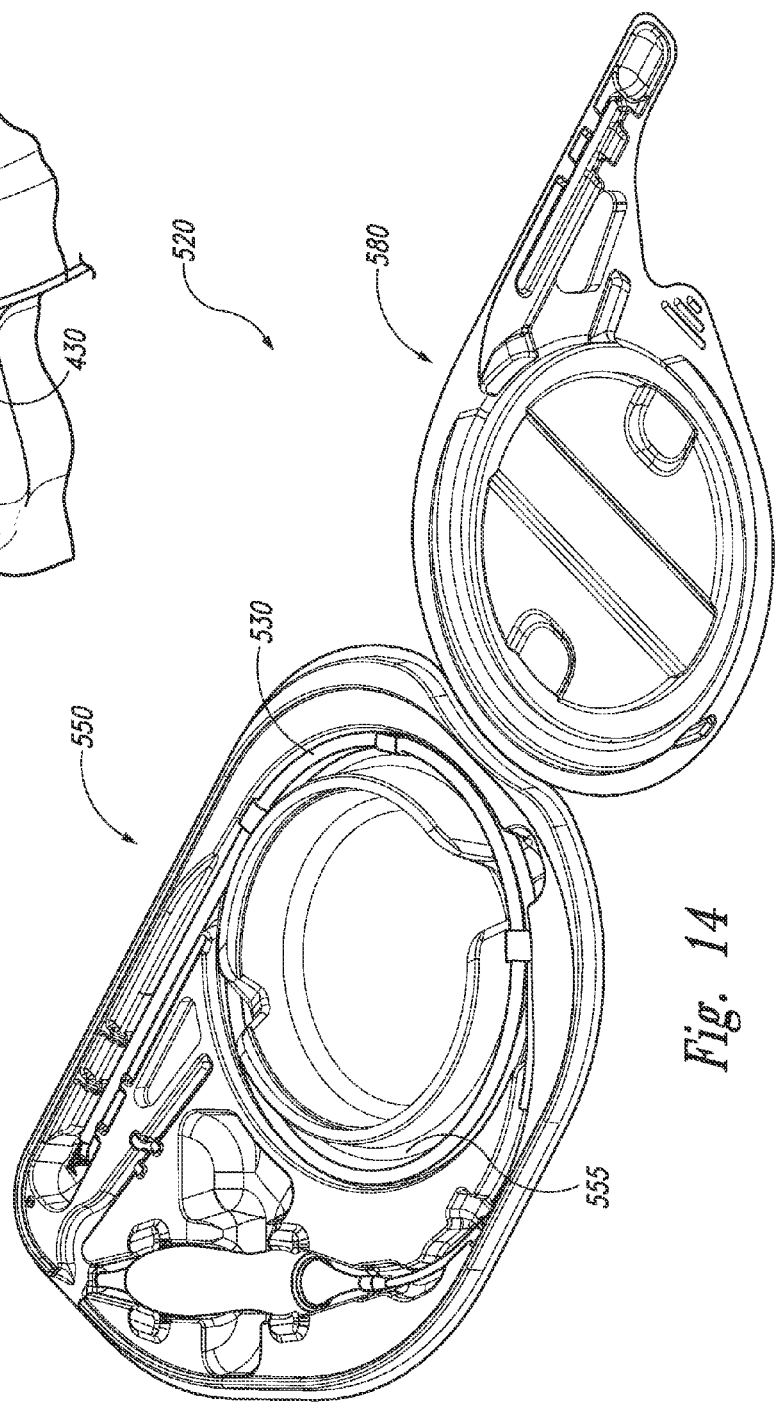

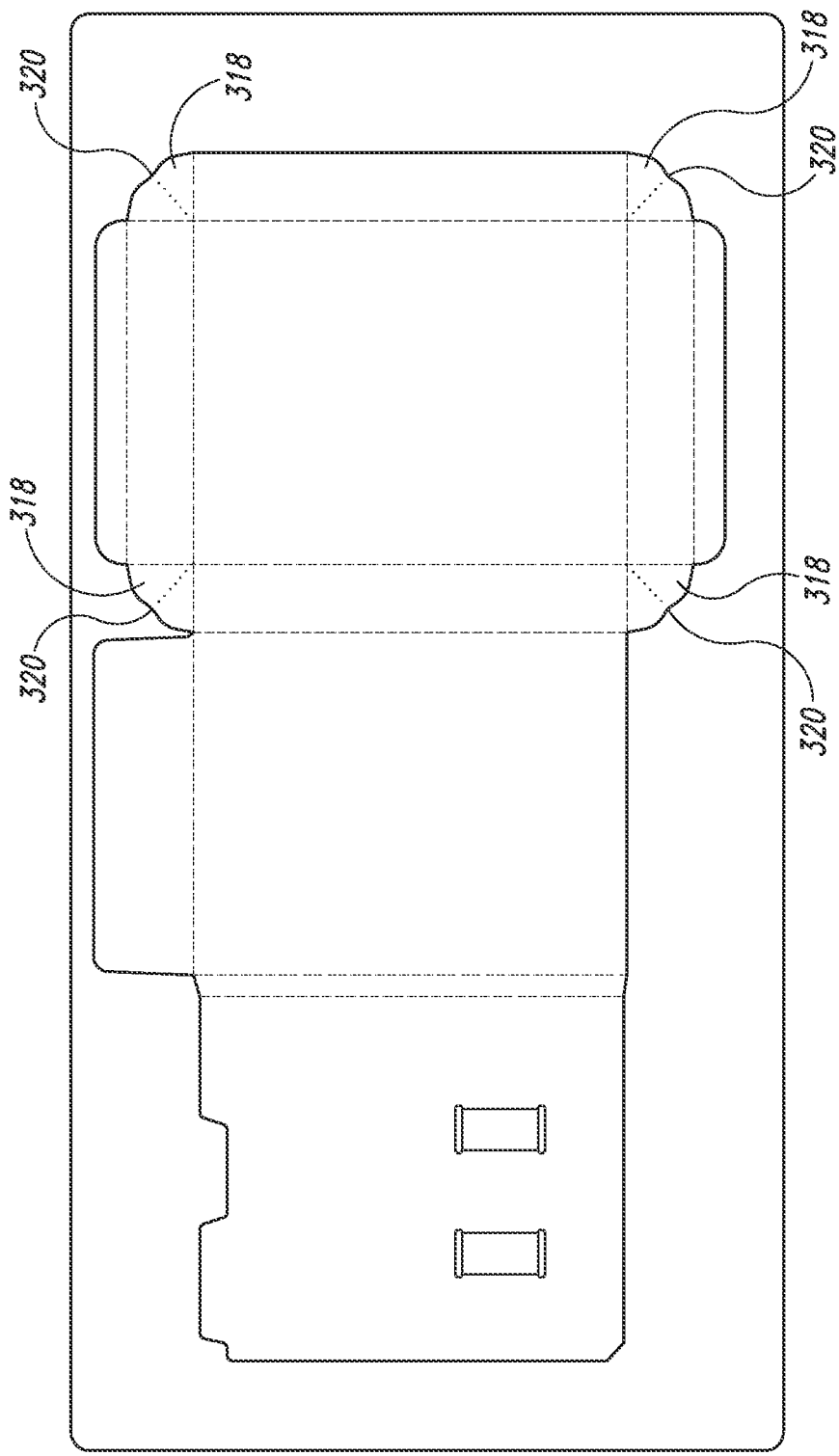

PACKAGING FOR CATHETER TREATMENT DEVICES AND ASSOCIATED DEVICES, SYSTEMS AND METHODS

CROSS REFERENCE TO RELATED APPLICATION(S)

The present application claims the benefit of and priority to U.S. patent application Ser. No. 13/840,484, filed Mar. 15, 2013, which claims the benefit of U.S. Provisional Patent Application No. 61/716,451, filed Oct. 19, 2012, the disclosures of which are incorporated herein by reference in their entireties.

TECHNICAL FIELD

The present technology relates generally to packaging for medical devices. In particular, various embodiments of the present technology are directed to packaging for catheter treatment devices configured to protect delicate portions of the catheter while maintaining the catheter in a relatively small package size.

BACKGROUND

Catheters are generally tubular medical devices configured for insertion into canals, vessels, passageways, lumens, or other suitable body cavities (e.g., to deliver energy to target tissue, to permit injection and/or withdrawal of fluids, to keep a passage open, etc.). Many advanced catheters are equipped with sophisticated therapeutic assemblies at distal end portions that are configured for delivery to various target treatment sites within the body. Such therapeutic assemblies are often delicate and complex components that require careful handling.

One example of such a device is a catheter treatment device having a multi-electrode array movable between a delivery or low-profile state (e.g., a generally straight shape) and a deployed state (e.g., a radially expanded, generally spiral/helical shape). The electrodes or energy delivery elements carried by the array can be configured to deliver energy (e.g., electrical energy, radio frequency (RF) electrical energy, pulsed electrical energy, thermal energy) to a target treatment site after being advanced via catheter along a percutaneous transluminal path (e.g., a femoral artery puncture, an iliac artery and the aorta, a radial artery, or another suitable intravascular path). The multi-electrode array can be sized and shaped so that the electrodes or energy delivery elements contact an interior wall of the target artery when the array is in the deployed (e.g., spiral/helical) state within the artery. The multi-electrode array of the catheter treatment device can be particularly delicate, and can be susceptible to damage during shipping and handling if not packaged appropriately. Conventional catheter packaging generally includes a sheath that contains the catheter within its internal lumen contained in long, cumbersome boxes that allow catheters to be shipped in a straight configuration.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIG. 6 is a front view in elevation of the catheter container of FIGS. 4 and 5.

FIG. 7 is an end view in elevation of the catheter container of FIGS. 4-6.

FIG. 9 is an isometric view of the catheter container of FIGS. 8A and 8B.

FIG. 13 is an enlarged partial view of the catheter package assembly of FIG. 12 illustrating a catheter clip attached to the catheter.

FIG. 14 is an isometric view of a catheter package assembly in accordance with another embodiment of the present technology.

FIG. 26 is a top plan view of a flat pattern of the box shown in FIGS. 25A and 25B.

DETAILED DESCRIPTION

The present technology is directed to packaging for catheter treatment devices, such as catheters including multi-electrode arrays. Because such arrays are so delicate, packaging that protects the array is required. The packaging designs described in this disclosure are configured to support and protect the multi-electrode array at the tip of the catheter during transit, while also providing a significantly smaller footprint than traditional packaging arrangements. The disclosed packaging arrangements are also expected to require less components/materials than many conventional catheter packages.

Specific details of several embodiments of the technology are described below with reference to FIGS. 1-31. Although various embodiments of catheter packaging are described herein with respect to catheter treatment devices including multi-electrode arrays, it will be appreciated that the disclosed technology may also be used for other types of catheters, particularly those that have delicate parts and/or therapeutic assemblies. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-31.

As used herein, the terms "distal" and "proximal" define a position or direction with respect to the treating clinician or clinician's control device (e.g., a handle assembly). "Distal" or "distally" are a position distant from or in a direction away from the clinician or clinician's control device. "Proximal" and "proximally" are a position near or in a direction toward the clinician or clinician's control device.

I. Catheter Package Assemblies

Figure 1:
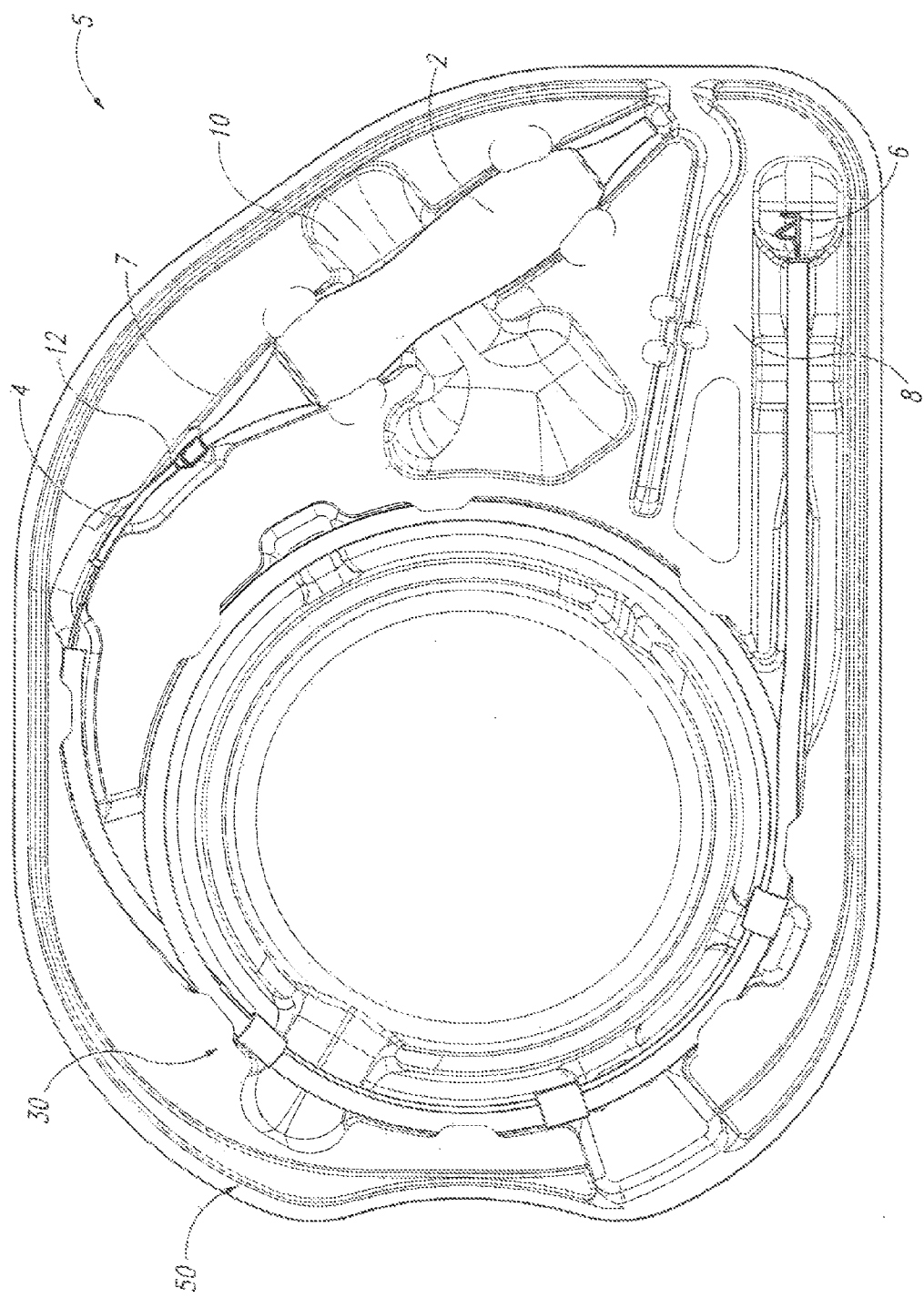
FIG. 1 is a top plan view of a catheter package assembly including a catheter container and a sheath assembly configured in accordance with an embodiment of the present technology.

FIG. 1 is a top plan view of a catheter package assembly 5 configured in accordance with an embodiment of the present technology. The catheter package assembly 5 includes a catheter container having a tray 50 and a coiled sheath assembly 30 disposed in the tray 50. The catheter package assembly 5 is configured to contain and protect a catheter 10. In the illustrated embodiment, for example, the catheter 10 includes a handle 2 and an elongated shaft 4 having a proximal end portion 7 and a distal end portion 8. The catheter 10 further includes a therapeutic assembly 6 (e.g., a multi-electrode array such as a spiral/helical tip or the like) at the distal end portion. As mentioned above, the multi-electrode array 6 of the catheter 10 is delicate and the catheter container is configured to protect this component during shipping and handling. Similarly, the shaft 4 is a very thin, delicate member that is protected by the sheath assembly 30 as shown. In some embodiments, the catheter 10 may also include a loading tool 12, which in this case is disposed towards the proximal end portion 7. The loading tool 12 is a tubular structure configured to slidably move along an outer surface of the shaft 4 and the multi-electrode array 6. The loading tool 12 is used to straighten the distal helical structure for back loading of a guide wire used to straighten the electrode during use. The catheter 10 may also include a cable assembly 15 (described in greater detail below with reference to FIG. 10A).

Figure 2:
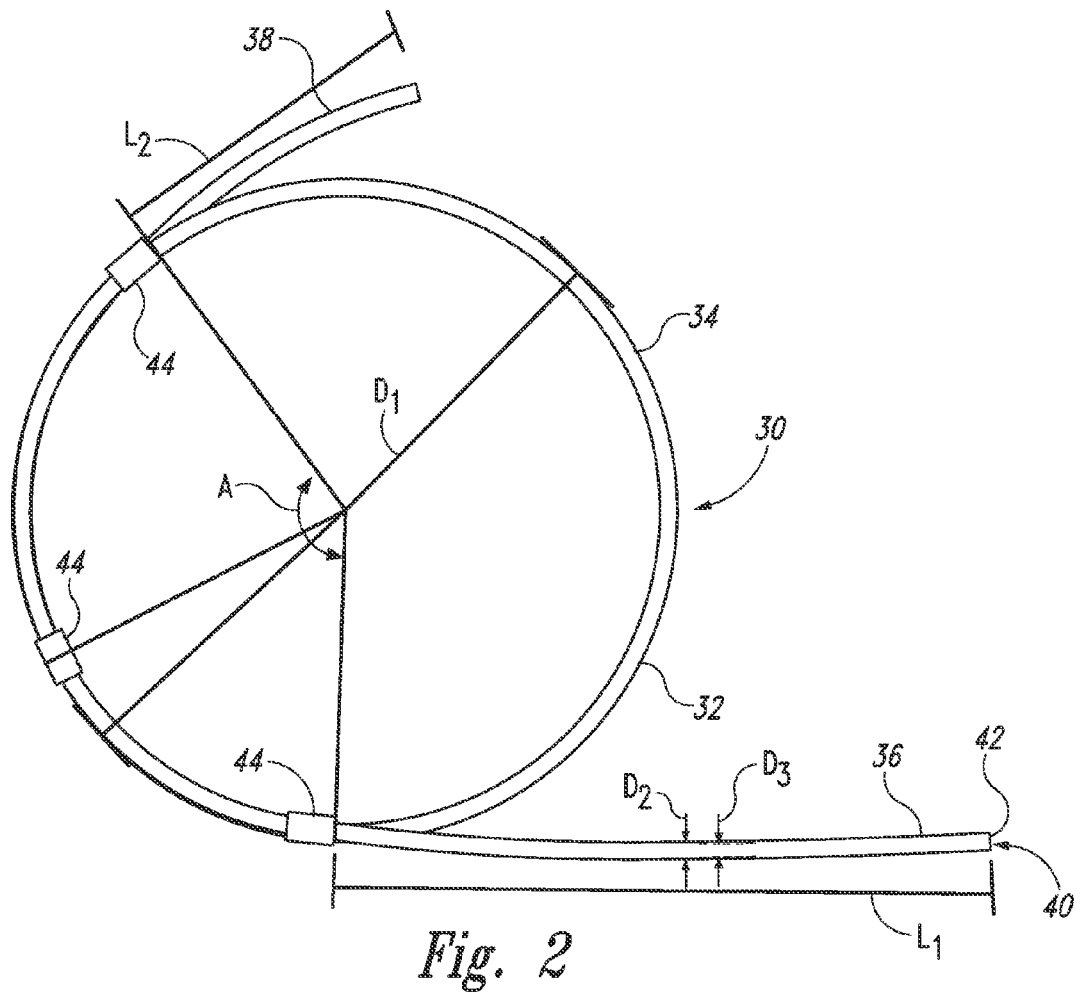
FIG. 2 is a top plan view of the sheath assembly of FIG. 1.

FIG. 2 is a top plan view of the sheath assembly 30 of FIG. 1. Sheath assembly 30 may also be referred to as a vertical dispensing hoop. In this embodiment, the sheath assembly 30 includes a length of tubing 32 arranged in a coil 34 with first and second tangent portions 36 and 38 extending tangentially therefrom. The coil portion 34 has a diameter $D_1$ (e.g., approximately 7.5 inches). The tubing 32 comprises a hollow member having an outside diameter $D_2$ and an inner diameter $D_3$. In one particular embodiment, $D_2$ is approximately 0.234 inch and $D_3$ is approximately 0.193 inch. In other embodiments, however, the diameter $D_1$, the inner diameter $D_3$, and/or the outer diameter $D_2$ may vary. The inner diameter $D_3$ defines a lumen 40 sized and configured to receive the shaft 4 of the catheter 10 (FIG. 1). The tubing 32 may be formed from a plastic material or another suitable material. In some embodiments, the tubing 32 may be transparent or translucent. In general, it may be desirable for the materials in the catheter packaging to be E-beam (electron-beam) sterilization compatible. In other embodiments, however, the tubing 32 may be composed of other types of materials and/or have different characteristics.

The first tangent portion 36 has a length $L_1$ (e.g., approximately 7.5 inches) extending from the coil portion 34. The first tangent portion 36 may also include a flared tip 42 to facilitate removal of the sheath assembly 30 from the catheter shaft 4 (FIG. 1). The second tangent portion 38 extends a distance $L_2$ (e.g., approximately 1.7 to 2.0 inches) from the coil portion 34. In this embodiment, the second tangent portion 38 extends around a radius of approximately 4 inches. In other embodiments, however, the first and/or second tangent portions 36 and 38 may have a different arrangement and/or different features.

Figure 3:
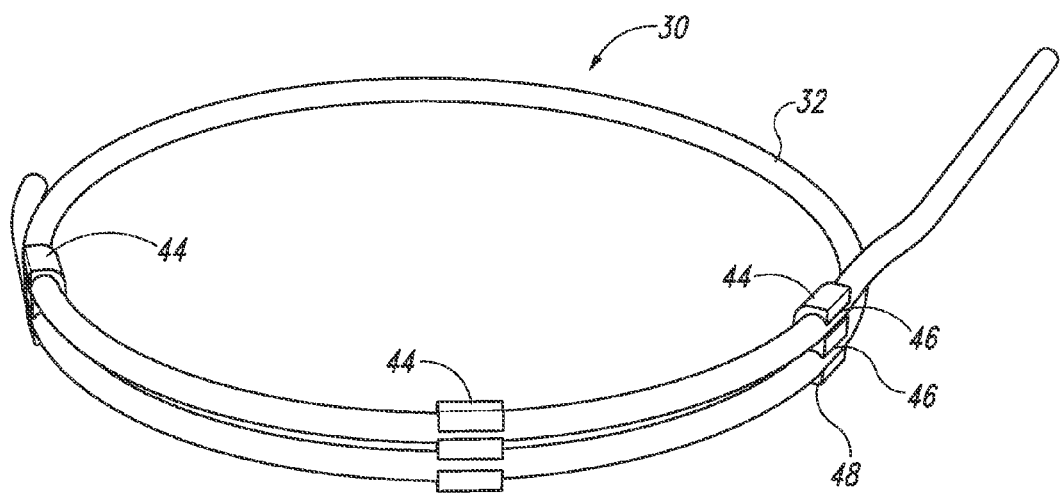
FIG. 3 is an isometric view of the sheath assembly of FIGS. 1 and 2.

Referring to FIGS. 2 and 3 together, the tubing 32 may be retained in the coil configuration by a plurality of clips 44. The clips 44, for example, are configured to engage the tubing 32 in a snap fit or press fit arrangement. In the illustrated embodiment, for example, the sheath assembly 30 comprises three clips 44 disposed approximately equiangularly from each other. More specifically, the outer two clips 44 are attached to the coiled tubing 32 and spaced apart by an angle A (e.g., approximately 145 degrees). A center clip 44 is disposed between the outer clips 44 (e.g., at an angle of approximately 72.5 degrees). It will be appreciated, however, that while the sheath assembly 30 includes one coil and multiple clips separated by particular angles, in other embodiments the sheath assembly 30 may have multiple coils, a different number of clips 44, and/or a different arrangement of clips 44.

As best seen in FIG. 3, the clips 44 can include a pair of grooves 46 sized and configured to grasp the tubing 32. An inner surface 48 of each groove 46 may include serrations to enhance the grip on tubing 32. Although the clips 44 in the illustrated embodiment comprise two grooves to accommodate a single coil, it will be appreciated that the clips 44 may be configured with additional grooves to retain multiple coils in a coiled configuration. The clips 44 may be comprised of a variety of suitable materials (e.g., high density polyethylene (HDPE) or another suitable plastic material).

Figure 4:
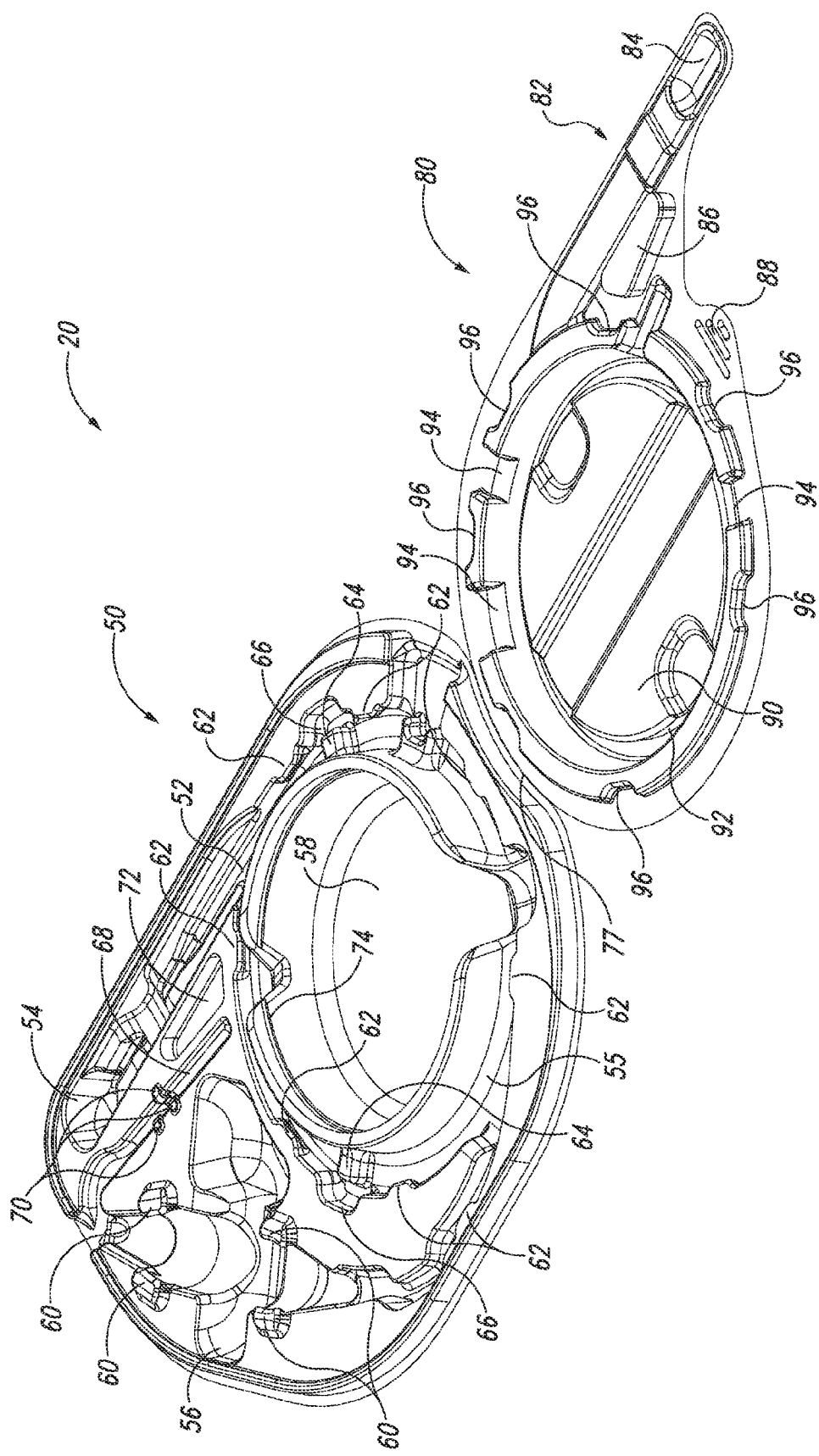
FIG. 4 is an isometric view of the catheter container of FIG. 1 in an open arrangement.
Figure 5:
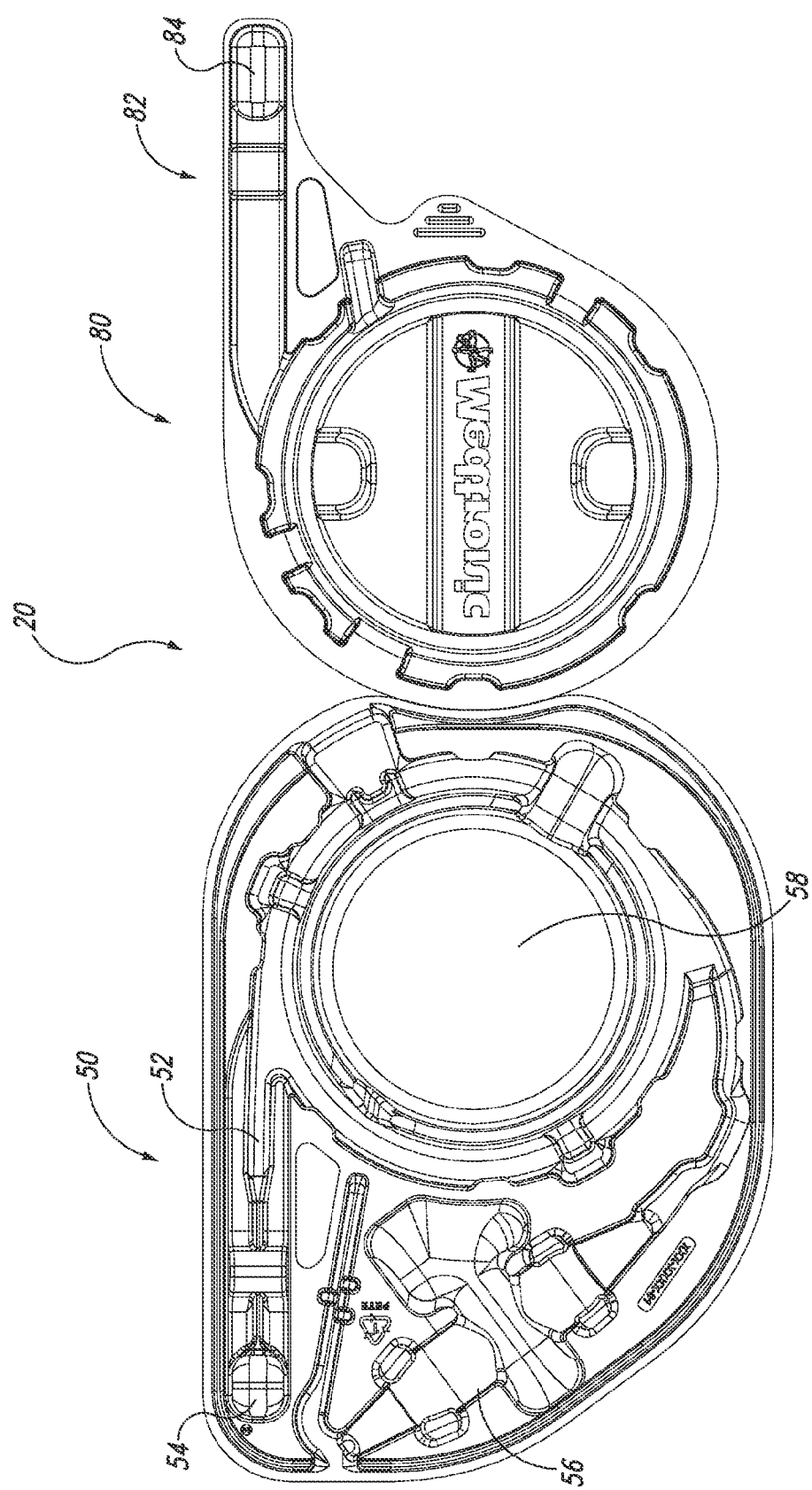
FIG. 5 is a top plan view of the catheter container of FIG. 4.

FIG. 4 is an isometric view of the catheter container 20 of FIG. 1 in an open arrangement, and FIGS. 5-7 are additional views of the catheter container 20. Referring to FIGS. 4-7 together (and with reference to the catheter 10 of FIG. 1), the catheter container 20 includes a tray 50 and a mating lid 80. The tray 50 includes a catheter channel 52 sized and configured to receive a catheter 10 therein. The channel 52 also includes a pocket 54 sized to receive the multi-electrode array 6 of the catheter 10. In the illustrated embodiment, for example, the pocket 54 is large enough to accommodate the delicate multi-electrode array 6 without the inner surface of the pocket making contact. The tray 50 also includes a handle pocket 56 configured to receive the handle 2 of the catheter 10. In the illustrated embodiment, the handle pocket 56 can also include a plurality of protrusions 60 arranged around a perimeter of the pocket 56 and positioned to releasably retain the handle 2 within the pocket 56. The protrusions 60, for example, may be formed into the material of the tray 50 and provide a snap fit or press fit arrangement for the handle 2.

Figure 10A:
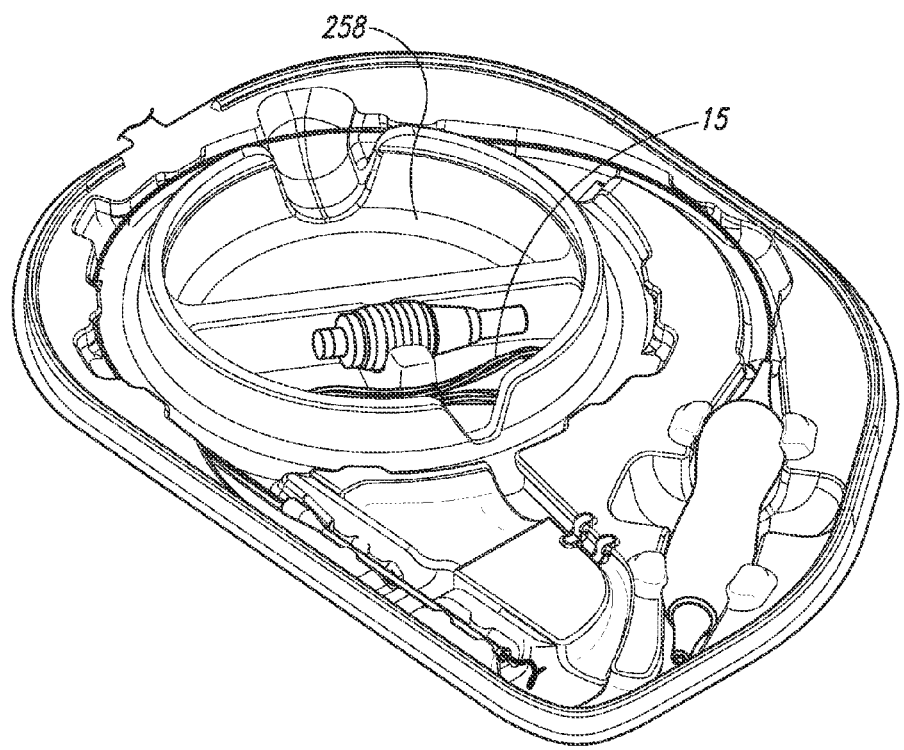
FIG. 10A is an isometric view of the catheter container of FIGS. 8A-9 with a representative catheter installed therein.

The catheter channel 52 can also include a coil groove 55 sized and configured to receive the sheath assembly 30 (FIGS. 1 and 2). A plurality of protrusions 62 may be arranged about the coil groove 55 and positioned to engage the sheath assembly 30 to removably retain the sheath assembly within the catheter container 20. In this embodiment, for example, the protrusions 62 are disposed on an outer diameter of the groove 55. A plurality of positioners 64 may be positioned on an inside diameter of the groove 55 and configured to cooperate with the protrusions 62 to locate the sheath assembly 30 around the groove 55. Further, opposite each positioner 64 is a relief 66 positioned to facilitate installation of the sheath assembly 30 into the tray 50. The tray 50 can also include a wire path 68 configured to receive the cable assembly 15 (FIG. 10A) therealong and a cable assembly cavity 58 located in or at least proximate to the middle of the coil groove 55 as shown. The cable path 68 can include a plurality of nubs 70 positioned to cooperate to grasp the cable assembly 15 (FIG. 10A).

The lid 80 of the catheter container 20 is configured to mate with the tray 50 to provide an enclosed container for at least a portion of the catheter 10 (FIG. 1). In the illustrated embodiment, for example, the lid 80 is constructed to cover only the sheath assembly 30 (and the shaft 4 contained therein) and the multi-electrode array 6. Accordingly, the lid 80 includes a channel cover portion 82 with an associated concave pocket cover 84. It will be appreciated from the arrangement illustrated in FIGS. 4-7 that channel cover 82 and pocket cover 84 correspond to channel 52 and pocket 54, respectively, of the tray 50. Thus, when installed, the lid 80 is positioned to cover the sensitive and delicate portions of the catheter 10 (FIG. 1). In some embodiments, the lid 80 can include a plurality of reliefs 96 that correspond to protrusions 62. The reliefs 96 provide clearance for protrusions 62 when the lid 80 is mated with the tray 50. Similarly, the lid 80 can include a plurality of notches 94 that correspond to the positioners 64. The notches 94 and positioners 64 may act in cooperation to index the lid 80 in the proper rotational position relative to the tray 50. In addition, the lid 80 may include a button 86 positioned to be inserted into a mating socket 72 located on the tray 50. The button 86 and socket 72 cooperatively provide additional indexing and location control for channel cover 82 and pocket cover 84. Furthermore, the button 86 may be configured to provide a friction fit when installed into the socket 72. In other embodiments, the lid 80 may include other features and/or have a different arrangement.

The lid 80 may be retained on the tray 50 by a latch feature 90. In this embodiment, for example, the latch feature 90 comprises a circular male feature including an undercut wall 92. The male latch feature 90 engages a corresponding latch feature 74 formed in the tray 50. In this embodiment, the latch feature 74 comprises a circular female feature that also includes an undercut wall. Cooperative latch features 90 and 74 may be snapped or pressed together to mate the lid 80 with the tray 50. The lid 80 may also include a tab 88 that extends over the pocket 56, thereby providing access to the edge of lid 80 to facilitate removal of the lid 80. In other embodiments, the latch features 74 and 90 may have a different configuration and/or the lid 80 may include a different number of latch features.

In the illustrated embodiment, the catheter container 20 is thermoformed as a single part. As shown in FIG. 4, however, the thermoformed components may optionally include a perforated seam 77 between the lid 80 and the tray 50 to facilitate separation of the two components. It should also be noted that the perforated seam 77 may be recessed help prevent any burrs or protrusions from contacting the pouch or sterile bag 312 (see FIG. 25B) in which the container is stored. In addition, the perimeter of the tray 50 may be raised to allow for a recessed fit between the lid and the tray when assembled together, thereby helping to prevent burrs or rough edges from contacting the sterile bag. As an alternative to a perforated seam, the lid 80 and tray 50 may be thermoformed as a single unit with a living hinge disposed therebetween such that the components form a clamshell arrangement. In other embodiments, the lid and tray may be formed as separate components. In one embodiment, for example, the catheter container 20 may be composed of polyethylene terephthalate glycol (PETG). In other embodiments, however, the catheter container 20 may be composed of other suitable materials (e.g., High Impact PolyStyrene (HIPS), HDPE, or the like).

II. Catheter Installation

Referring to FIGS. 1 and 4 together, now that various features of embodiments of the catheter packaging assembly 5 have been described, installation of the catheter 10 into the catheter packaging assembly 5 in accordance with one embodiment of the present technology may be appreciated. First, the insertion tool 12 is installed on the catheter shaft 4 and located near handle 2 at the proximal end portion 7 of the shaft 4. The shaft 4 may then be threaded through the sheath assembly 30. Once the shaft 4 of the catheter 10 has been disposed in the sheath assembly 30, the sheath assembly 30 may be snapped into the coil groove 55 and retained therein in the desired orientation by the protrusions 62 and positioners 64.

Meanwhile, the handle 2 can be positioned in the pocket 56 and retained therein by the protrusions 60. The cable assembly 15 may be installed into the cable pathway 68 and retained therein by the nubs 70. The associated components of the cable assembly 15, such as the cable and connector, may also be positioned in the cable cavity 58. The lid 80 may be removed from the tray portion 50 and positioned over the coil groove 55 as well as the catheter channel 52 and the pocket 54. In an another embodiment, the lid 80 may be hingedly rotated about a living hinge and positioned over the coil groove 55 as well as the catheter channel 52 and the pocket 54. Reliefs 96 and notches 94 can be aligned with the protrusions 62 and positioners 64, respectively. Finally, the cooperative latch feature 90 may be snapped into the associated female feature 74 of the tray 50, and the button 86 may be engaged with the socket 72 such that the lid 80 covers the most sensitive/delicate portions of the catheter 10. The catheter packaging assembly 5 may then be sealed in a sterile bag and inserted into a protective box (described below with reference to FIGS. 24A-26) for packaging and/or shipping. In other embodiments, it will be appreciated that one or more steps of the foregoing installation process may be modified and/or eliminated.

Figure 8A:
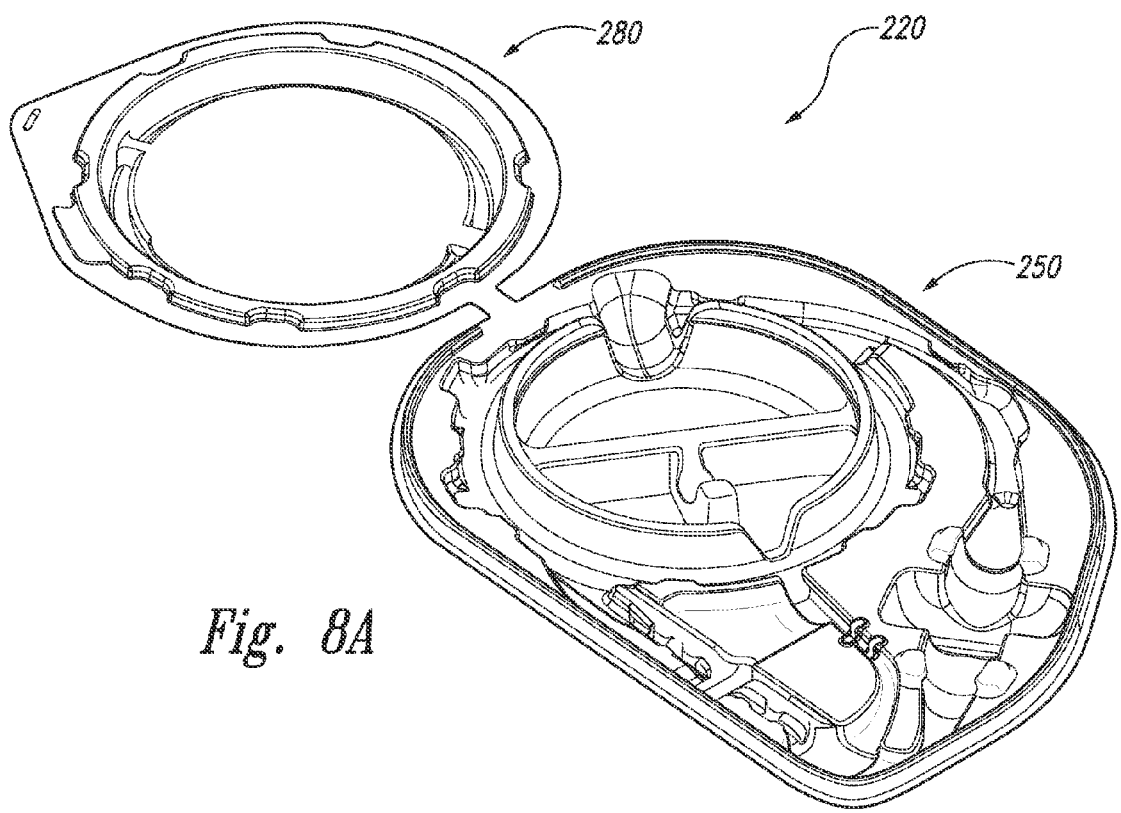
FIG. 8A is an isometric view of a catheter container configured in accordance with another embodiment of the present technology.
Figure 8B:
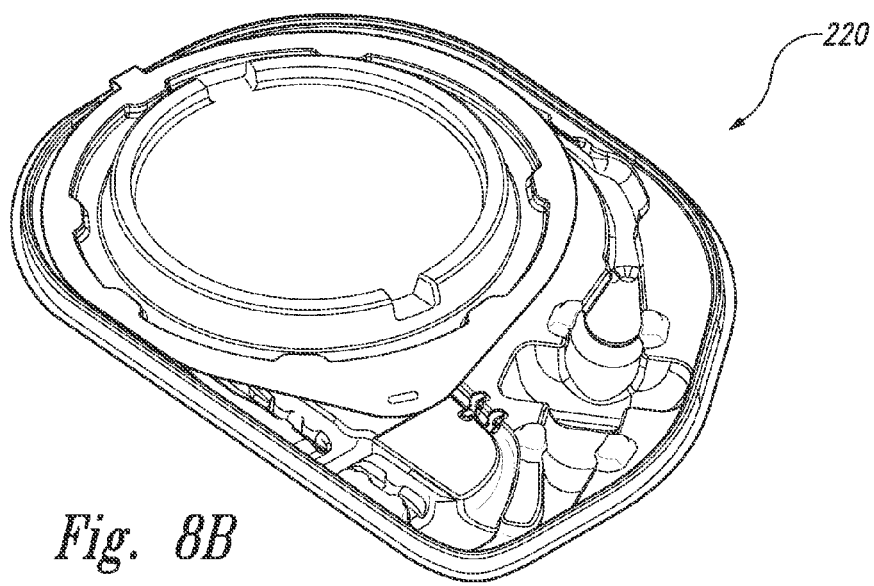
FIG. 8B is an isometric view of the catheter container of FIG. 8A in a closed configuration.

III. Additional Embodiments of Catheter Containers for Catheter Package Assemblies FIGS. 8A-9 illustrate a catheter container 220 configured in accordance with another embodiment of the present technology. In FIGS. 8A and 9, for example, the catheter container 220 is shown in the open arrangement and includes a tray 250 and a mating lid 280, while FIG. 8B illustrates the catheter container 220 in a closed arrangement. As best seen in FIG. 9, the lid 280 is sized and configured to only cover a coil portion of a catheter (not shown) carried by the container 220, and does not extend to cover a distal end portion of the catheter. As further seen in FIG. 9, it will be appreciated that the catheter container 220 is not configured for use with an additional sheath assembly (such as the sheath assembly 30 described above with reference to FIGS. 1-7). In this embodiment, the cable cavity 258 is divided to provide a pocket for the cable assembly 15 as well as other accessories.

Figure 10B:
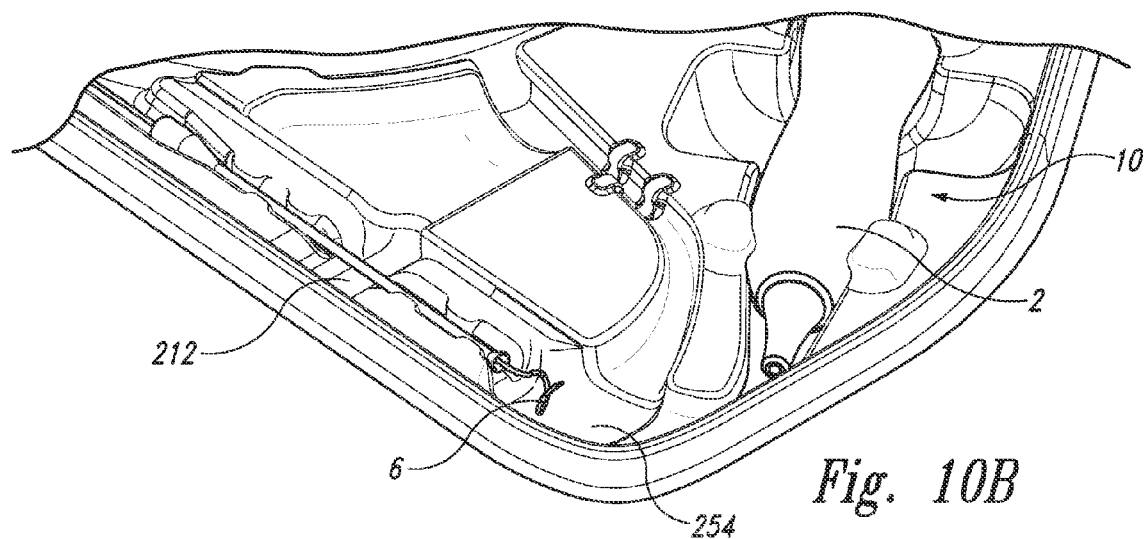
FIG. 10B is an enlarged partial view of the catheter container illustrating a distal end of the catheter installed therein.

In the illustrated embodiment, the catheter shaft 4 is retained in a coiled state by a plurality of channel protrusions 262. The catheter container 220 can be formed with pockets 254, 256 shaped to hold the catheter 10 in a coiled configuration as shown in FIGS. 10A and 10B. Light friction features in the form of protrusions 262 may be provided that allow the catheter 10 to be snapped into the pockets 254, 256 with minimal force, but will prevent the catheter 10 from shifting and/or falling out of the pockets 254, 256 during transit. The friction features holding the catheter body may also be configured to hold various loops of catheter length, i.e. could allow for holding longer length catheters that would be looped in several rotations as opposed to a shorter length catheter that would only form a single loop.

In the embodiment illustrated in FIGS. 8A-10B, the lid 280 is connected to the tray 250 with a living hinge 277 (FIG. 9) such that the components form a clamshell arrangement. In one embodiment, for example, the clamshell may be thermoformed as a single piece structure with a living hinge holding the lid 280 to the tray 250. One feature of this arrangement is that the single piece construction is expected to help minimize the number of stock-keeping units (SKUs) to be managed. In another embodiment, however, the hinge could be perforated such that the lid 280 can be torn from the tray 250 as a final manufacturing step. The lid 280 could then be used as a separate piece from the tray 250. In still further embodiments, the catheter container 220 may have a different arrangement and/or different features.

As best seen in FIG. 10B, the catheter 10 can be provided with a loading tool 212. In this arrangement, the loading tool 212 comprises a sliding sleeve carried by the catheter 10 and configured to slide up and down the length of an outside surface of the catheter shaft 4. Loading tool 212 is used to straighten the distal helical structure for back loading of a guide wire used to straighten the electrode during use. The loading tool 212 can be positioned near a distal section of the catheter 10 and held by the friction features of the catheter container to hold the catheter in place. In this arrangement, the loading tool 212 is expected to provide additional support to the distal end portion of the catheter 10. In another embodiment, an additional, optional feature (e.g., end stop feature 662 in FIG. 16) could be added to the tray 250 that works as a hard stop to prevent the loading tool 212 from inadvertently sliding towards the multi-electrode array 6 of the catheter 10 and straightening out the spirally-/helically-shaped array during shipping. Because the multi-electrode array 6 may be composed of shape memory material, shipping the catheter with the multi-electrode array 6 in a straightened configuration could alter the array's desired expanded configuration. Accordingly, a pocket 254 surrounding the multi-electrode array 6 is formed to be large enough so that the array 6 can be shipped in its expanded arrangement and protected from making damaging contact with an inner surface of the packaging.

Figure 11:
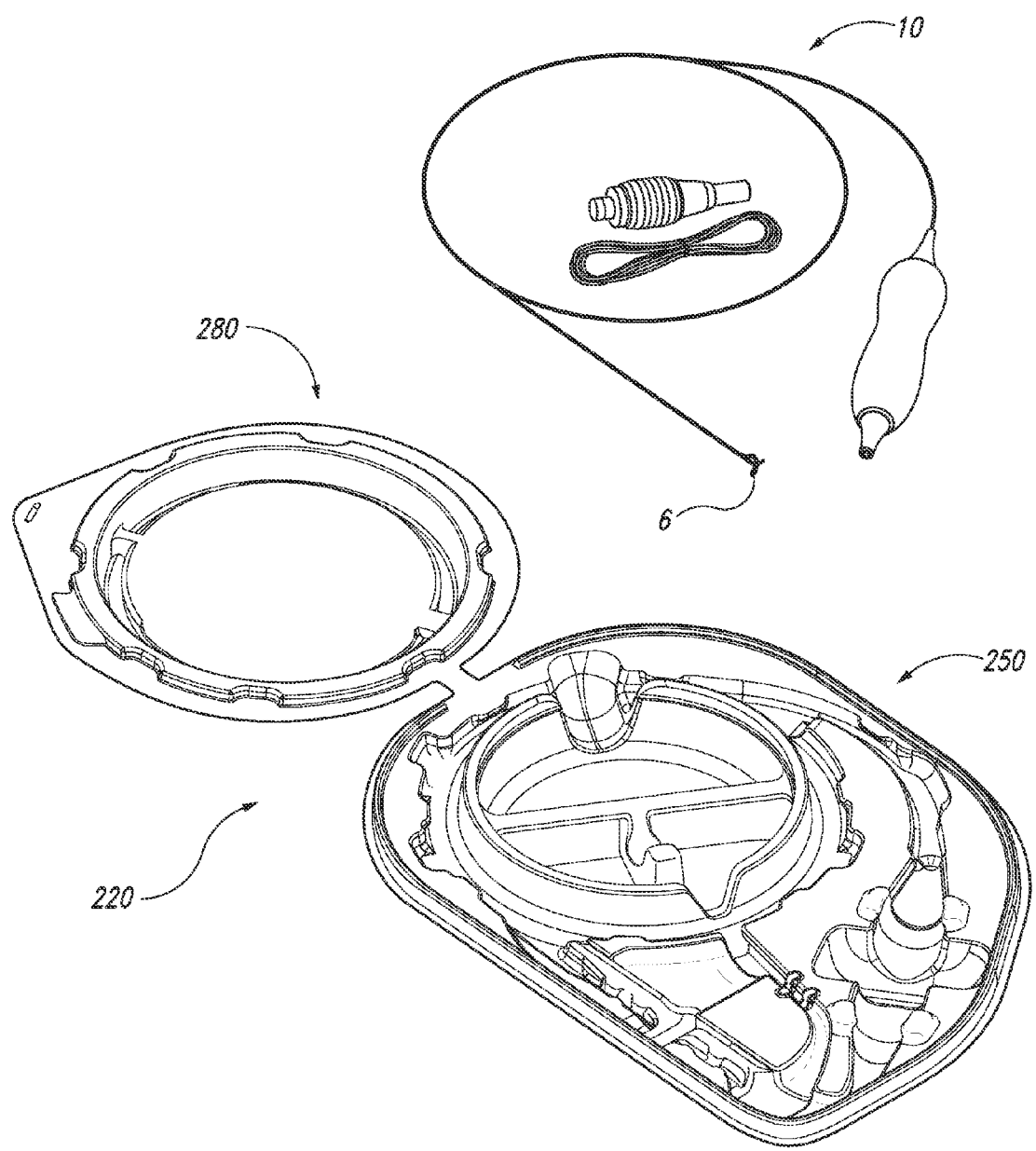
FIG. 11 is an exploded isometric view of the catheter container and catheter of FIG. 10A.

Another feature of the disclosed catheter packaging assemblies is that the cable assembly 15 may be removed from the packaging and plugged into an external energy generator (not shown) for testing while the remainder of the cable and catheter remain contained within the packaging. Further, as shown in FIG. 11, when the catheter is removed from the catheter container 220, it is configured to remain in a coiled configuration. This arrangement may be desirable such that the user can unravel the catheter in its natural state.

Figure 12:
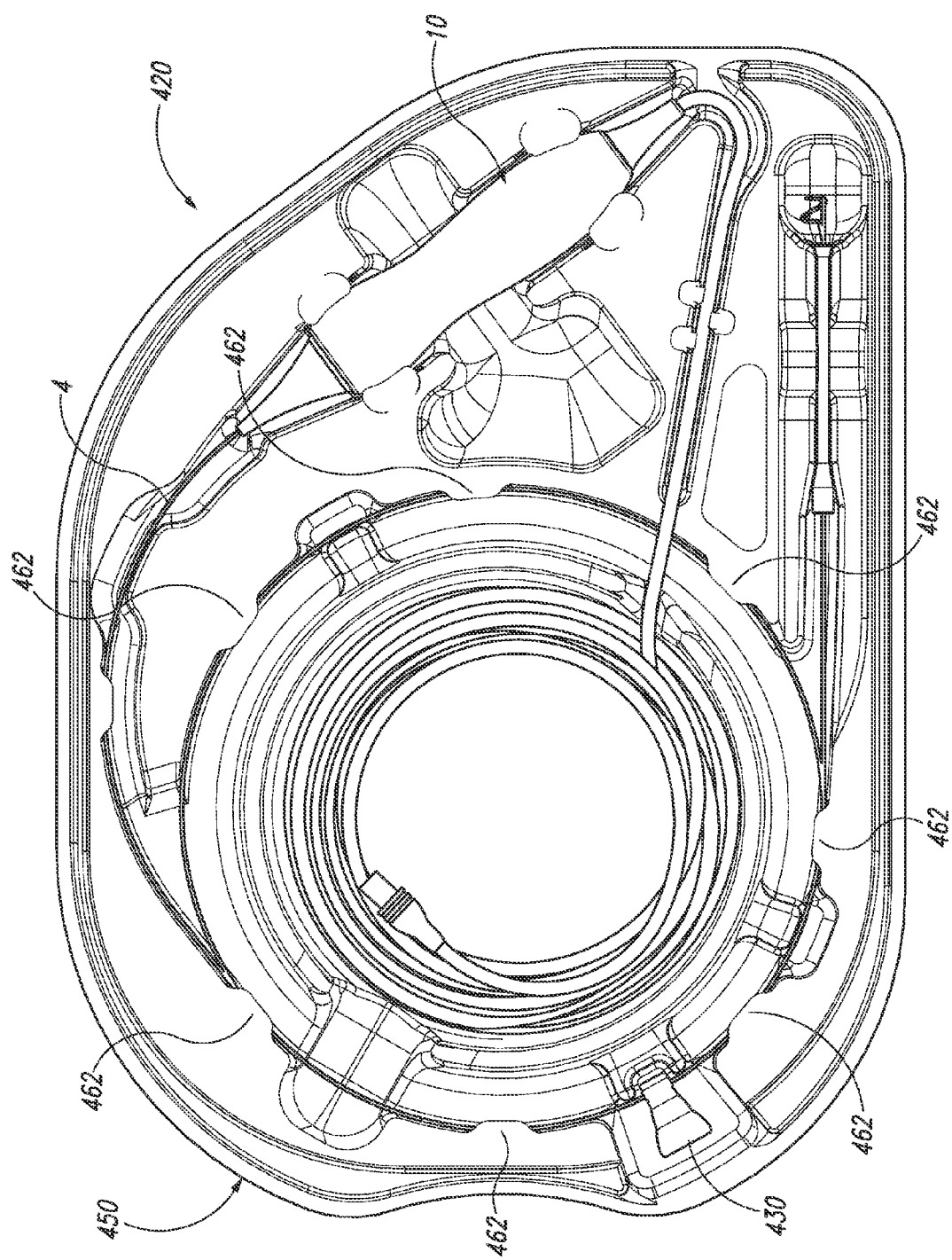
FIG. 12 is a top plan view of a catheter package assembly in accordance with another embodiment of the present technology.

FIGS. 12 and 13 illustrate a catheter container 420 configured in accordance with another embodiment of the present technology. In FIG. 12, for example, the catheter container 420 includes a tray 450 and a mating lid (not shown) that are similar to the tray and lid described above with respect to FIGS. 5-7. As further seen in FIG. 12, it will be appreciated that the catheter container 420 does not use an additional sheath assembly (such as the sheath assembly 30 described above with reference to FIGS. 1-7). Instead, the shaft 4 of the catheter 10 is retained in a coiled state by at least one catheter clip 430 and a plurality of channel protrusions 462. As best seen in FIG. 13, for example, the catheter clip 430 is disposed in a mating clip pocket 495 formed in tray 450.

FIG. 14 illustrates a catheter package assembly including a container 520 configured in accordance with still another embodiment of the present technology. The catheter container 520 includes a tray 550 and a mating lid 580 similar to the tray and lid described above with respect to FIGS. 5-7. In this embodiment, however, coil groove 555 does not include any protrusions (such as protrusions 62 described above with reference to FIGS. 1-7). Rather, in this embodiment the sheath assembly 530 is retained in the catheter container 520 by the lid 580.

Figure 15:
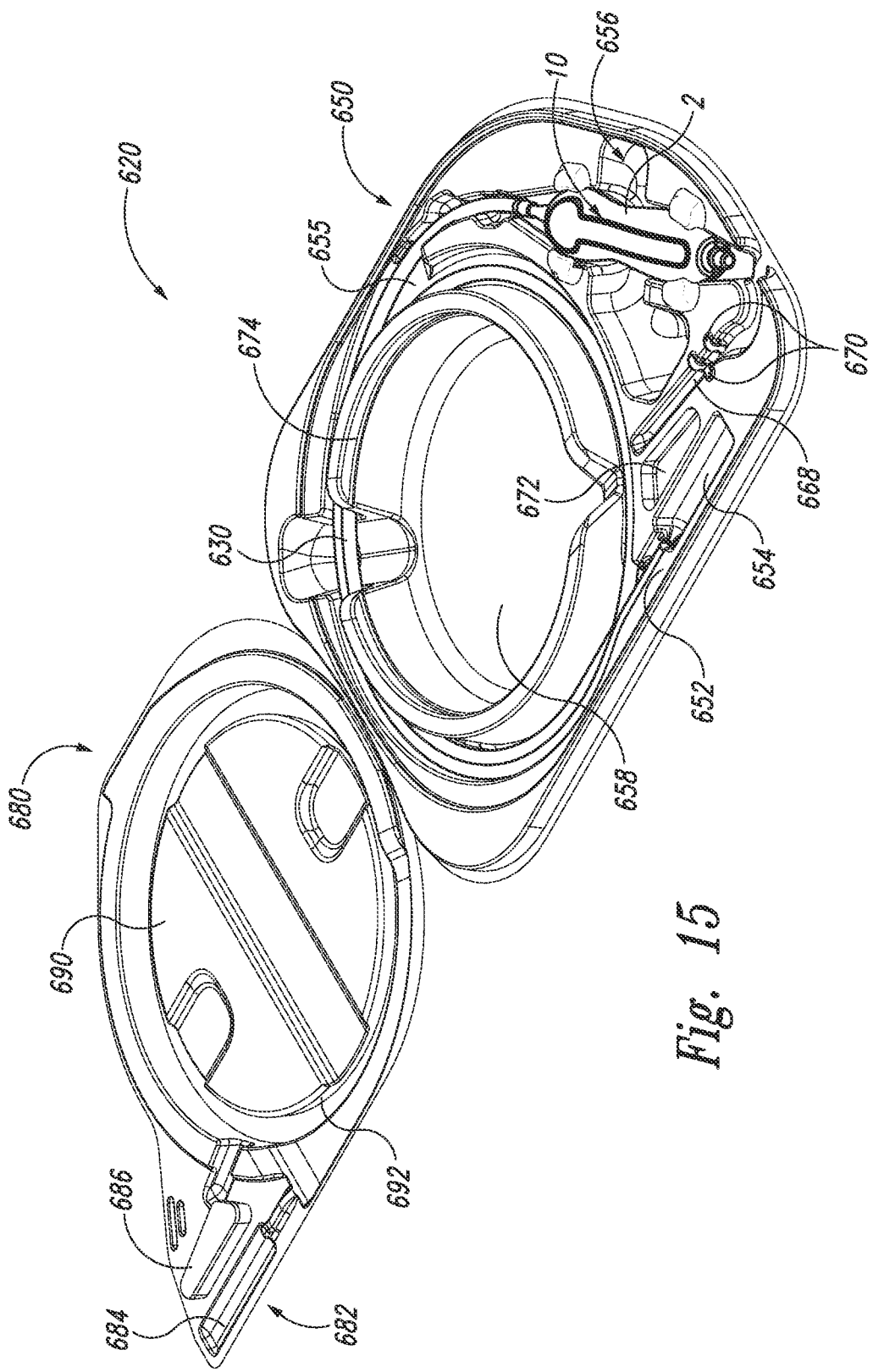
FIG. 15 is an isometric view of a catheter package assembly configured in accordance with another embodiment of the present technology.
Figure 16:
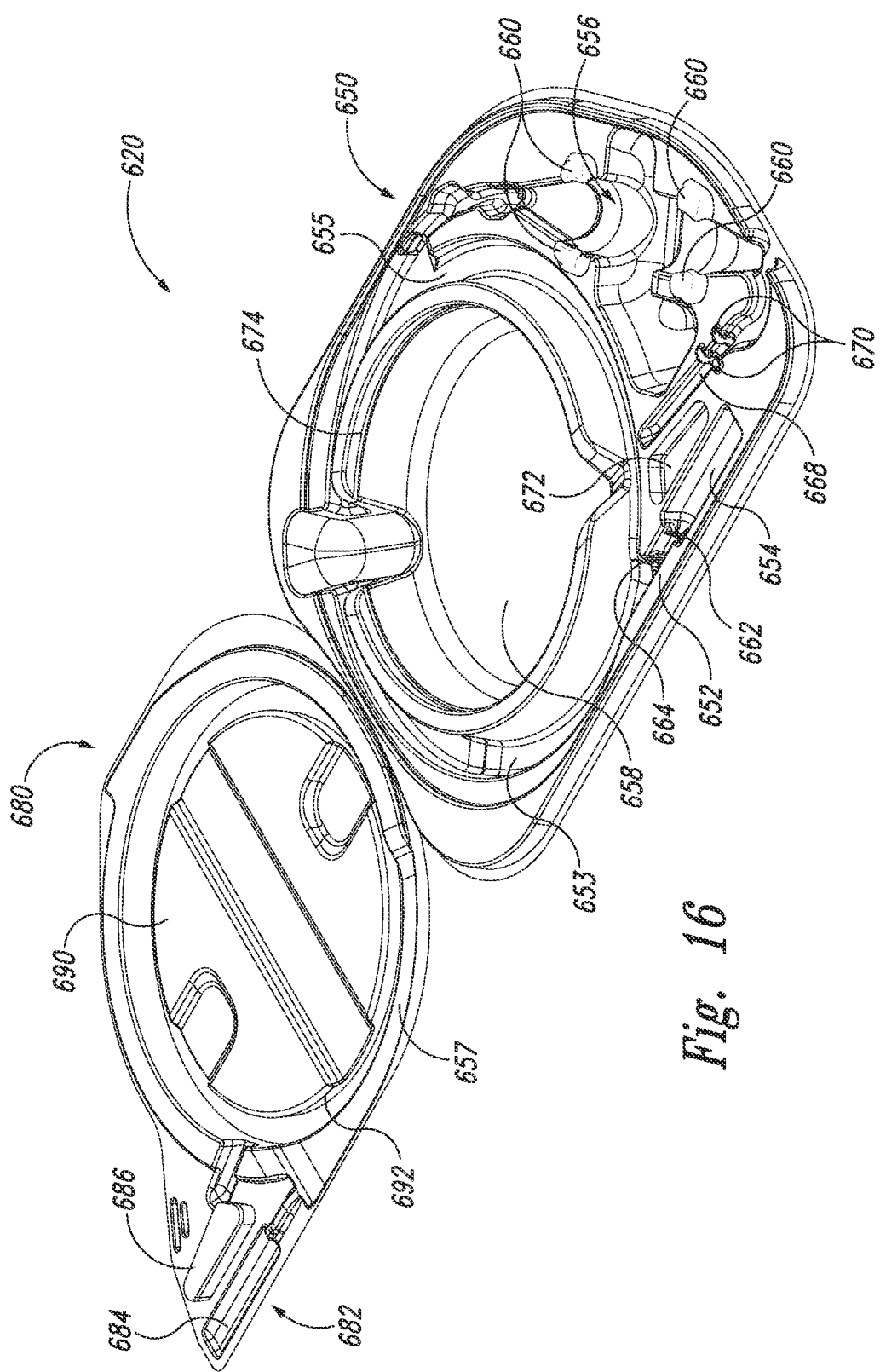
FIG. 16 is an isometric view of the catheter package assembly of FIG. 15.
Figure 17:
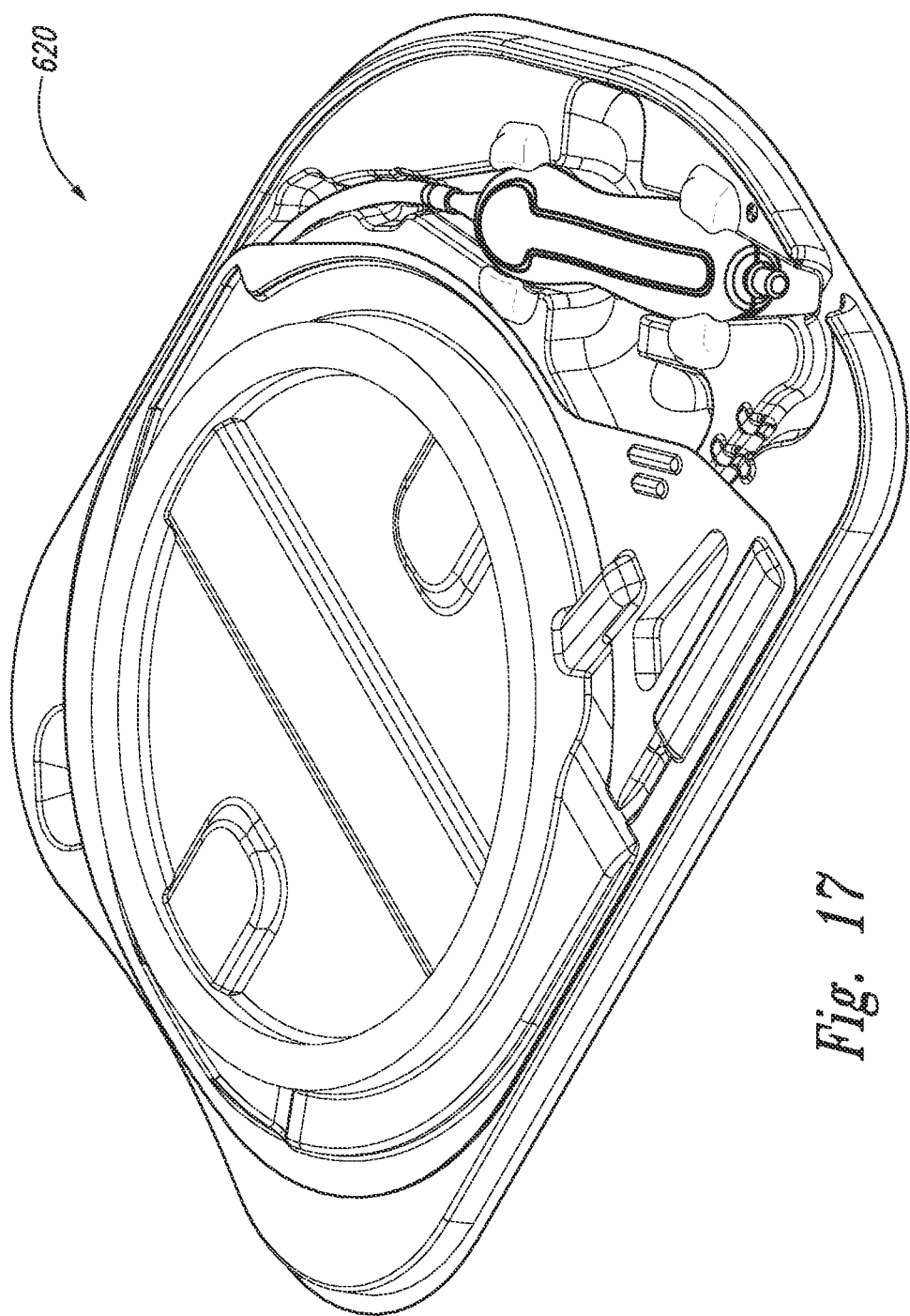
FIG. 17 is an isometric view of the catheter package assembly shown in FIG. 15 in a closed configuration.
Figure 18:
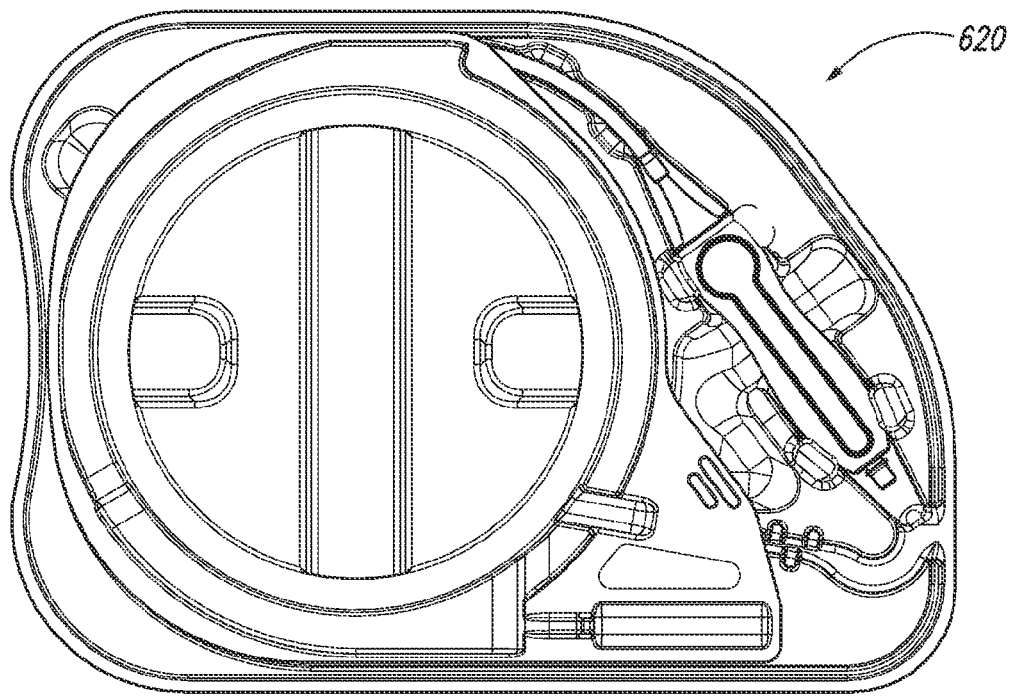
FIG. 18 is a top plan view of the catheter package assembly shown in FIG. 17.
Figure 19:
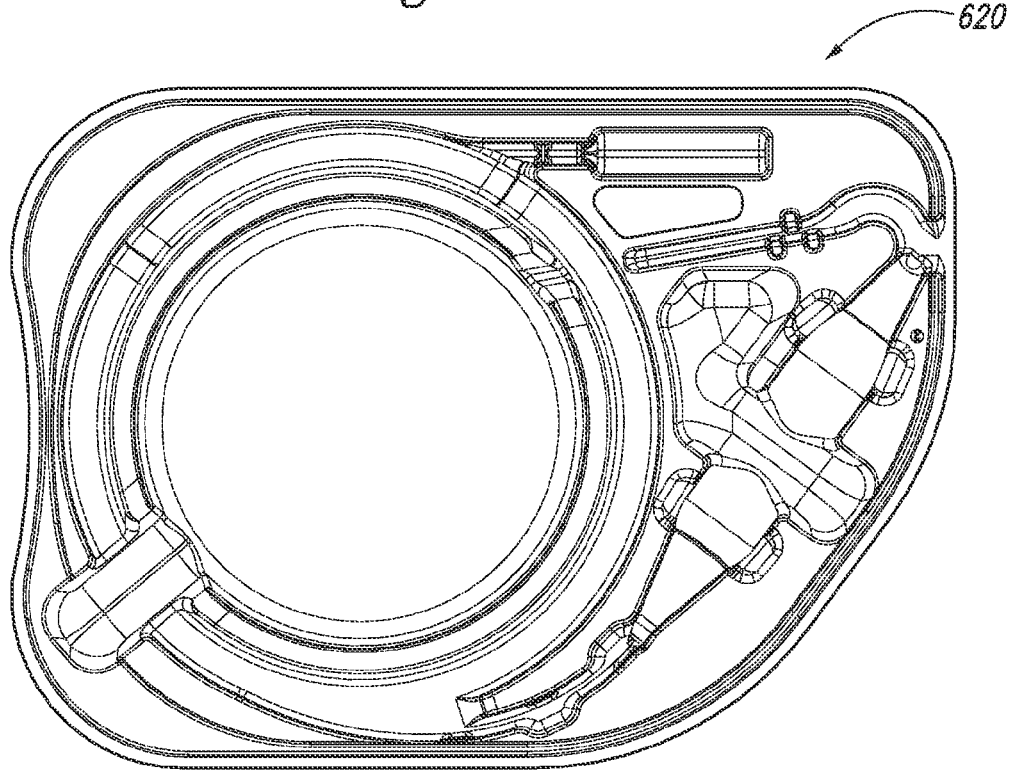
FIG. 19 is a bottom plan view of the catheter package assembly shown in FIG. 17.
Figure 20:
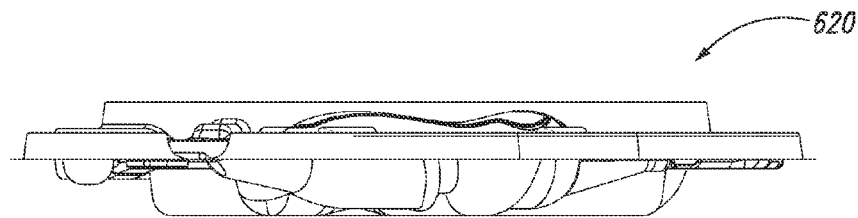
FIG. 20 is a right side view in elevation of the catheter package assembly shown in FIG. 17.
Figure 21:
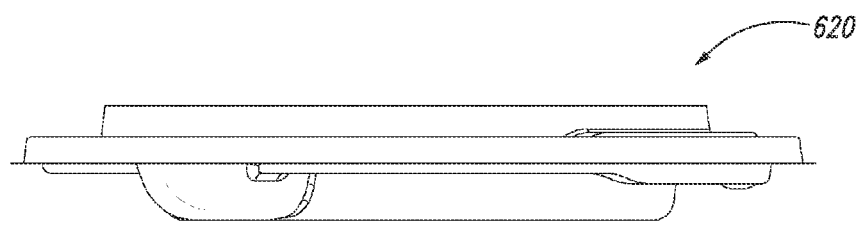
FIG. 21 is a left side view in elevation of the catheter package assembly shown in FIG. 17.
Figure 22:
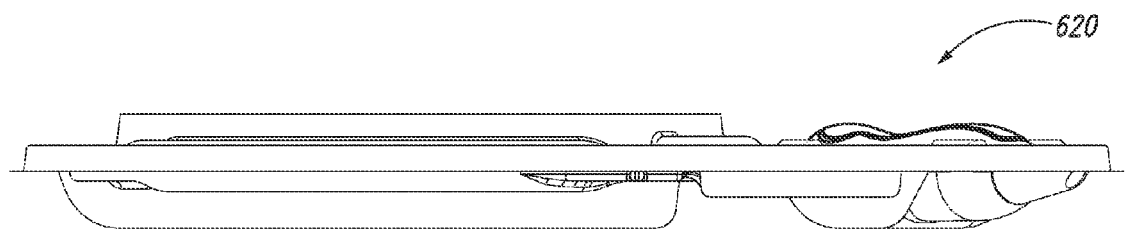
FIG. 22 is a front side view in elevation of the catheter package assembly shown in FIG. 17.
Figure 23:
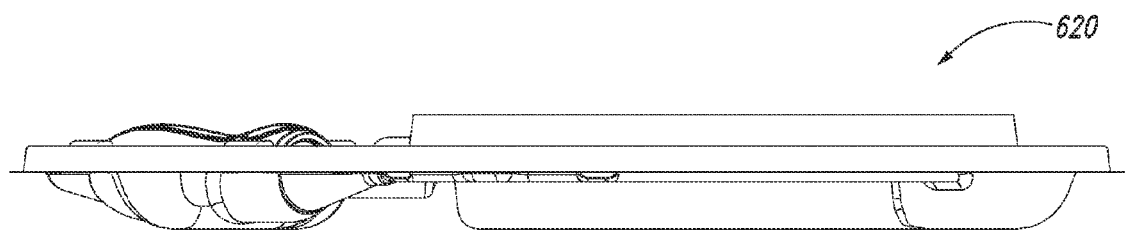
FIG. 23 is a back side view in elevation of the catheter package assembly shown in FIG. 17.

FIGS. 15-23 illustrate a catheter container 620 in accordance with a further embodiment of the present technology. More specifically, FIGS. 15 and 16 show the catheter container 620 in an open configuration, while FIGS. 17-23 show the catheter container 620 in a closed configuration. With reference to FIGS. 15 and 16, the catheter container 620 includes a tray 650 and a mating lid 680. The tray 650 includes a catheter channel 652 sized and configured to receive the catheter 10 therein. Further, the channel 652 includes a pocket 654 sized to receive the multi-electrode array 6 of the catheter 10. The tray 650 also includes a handle pocket 656 configured to receive the handle 2 of the catheter 10. In the illustrated embodiment, the handle pocket 656 can also include a plurality of protrusions 660 arranged around a perimeter of the pocket 656 and positioned to releasably retain the handle 2 within the pocket 656.

The catheter channel 652 can also include a coil groove 655 sized and configured to receive a sheath assembly 630. In this embodiment, the sheath assembly 630 is a coil of tubing that is bonded, welded, or otherwise secured to itself to retain the tubing in a coiled configuration. As best shown in FIG. 16, coil groove 655 includes a recessed portion 653 and the lid 680 includes a mating recessed portion 657. Thus, sheath assembly 630 is held secure in the coil groove 655 against the lid 680, except the recessed portions 653 and 657 provide space for the sheath coil to overlap. Proximate the pocket 654, the channel 652 includes a retainer feature 664 and an end stop feature 662. The sheath assembly 630 is retained in the channel 652 against the end stop feature 662 by the retainer feature 664. Accordingly, the end of the sheath assembly 630 is securely located relative to the pocket 654 in order to help prevent the multi-electrode array from touching the inside of pocket 654 during assembly and shipment.

The tray 650 can also include a wire path 668 configured to receive the cable assembly 15 (FIG. 10A) therealong and a cable assembly cavity 658 located in or at least proximate to the middle of the coil groove 655 as shown. The cable path 668 can include a plurality of nubs 670 positioned to cooperate to grasp the cable assembly 15 (FIG. 10A).

The lid 680 of the catheter container 620 is configured to mate with the tray 650 to provide an enclosed container for at least a portion of the catheter 10. In the illustrated embodiment, for example, the lid 680 is constructed to cover only the sheath assembly 630 and the multi-electrode array 6. Accordingly, the lid 680 includes a channel cover portion 682 with an associated concave pocket cover 684. When installed, the lid 680 is positioned to cover the sensitive and delicate portions of the catheter 10. The lid 680 may include a button 686 positioned to be inserted into a mating socket 672 located on the tray 650. The button 686 and socket 672 cooperatively provide indexing and location control for the channel cover 682 and the pocket cover 684. Furthermore, the button 686 may be configured to provide a friction fit when installed into the socket 672. In other embodiments, however, the lid 680 may include other features and/or have a different arrangement.

The lid 680 may be retained on the tray 650 by a latch feature 690. In this embodiment, for example, the latch feature 690 is a circular male feature that includes an undercut wall 692. The male latch feature 690 engages a corresponding female latch feature 674 formed in the tray 650. In this embodiment, the latch feature 674 is a circular female feature that also includes an undercut wall. Cooperative latch features 690 and 674 may be snapped or pressed together to mate the lid 680 with the tray 650. In other embodiments, the latch features 674 and 690 may have a different configuration and/or the lid 680 may include a different number of latch features.

Figure 27:
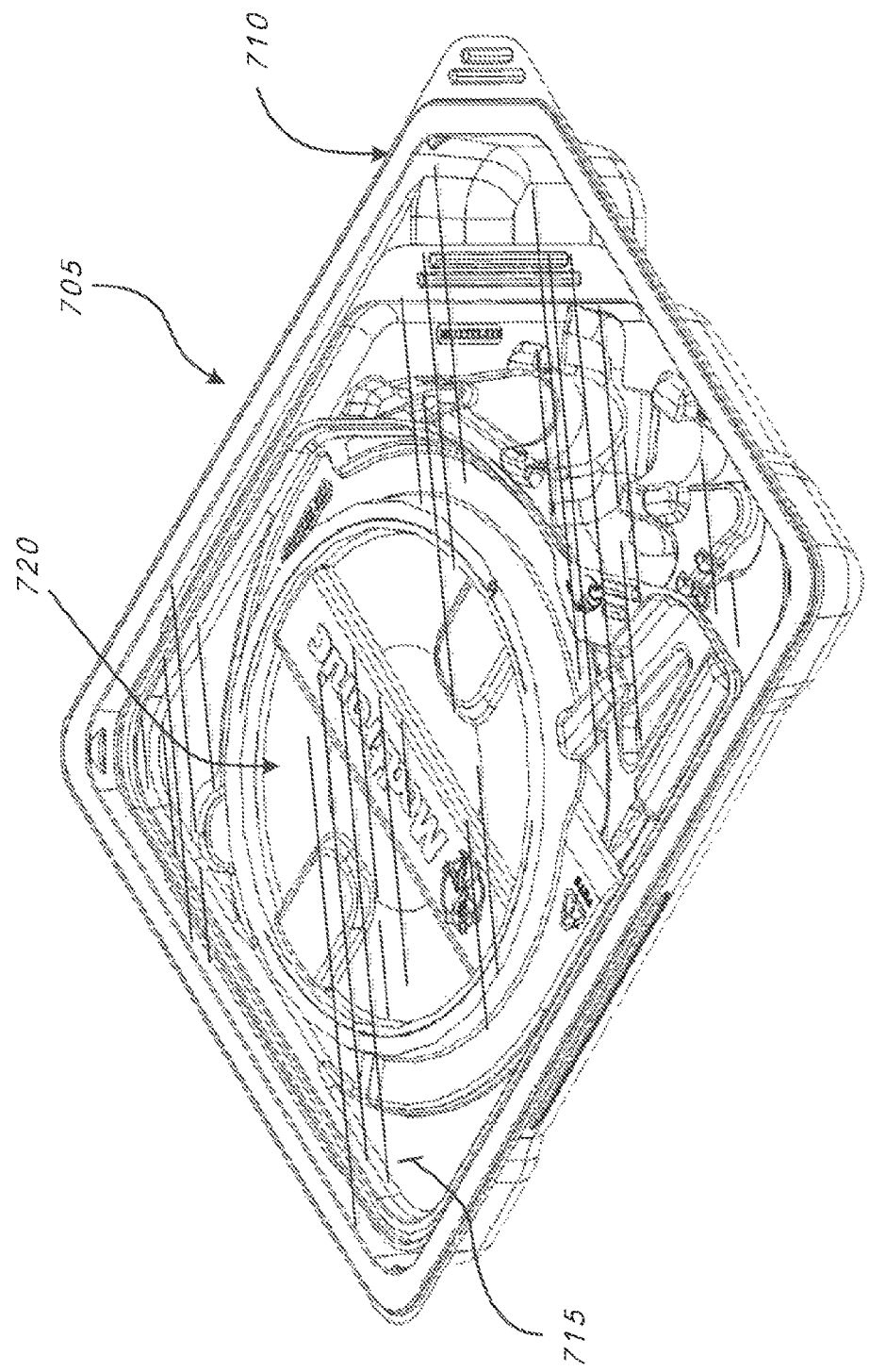
FIG. 27 is an isometric view of a catheter package assembly configured in accordance with another embodiment of the present technology.

FIG. 27 illustrates a catheter package assembly 705 in accordance with another embodiment of the present technology. Cather package assembly 705 includes a catheter container 720, similar to that described above with respect to FIGS. 15-23, a blister shell 710 configured to contain the catheter container 720, and a lidding sheet 715 to seal the catheter container 720 inside the blister shell 710. Thus, catheter container 720 is packaged in a blister pack comprising the blister shell 710 and the lidding sheet 715. Sealing the catheter container 720 inside the blister pack may eliminate the need for a pouch or header bag, which can simplify the design in terms of end user interaction and sterile presentation.

Figure 28:
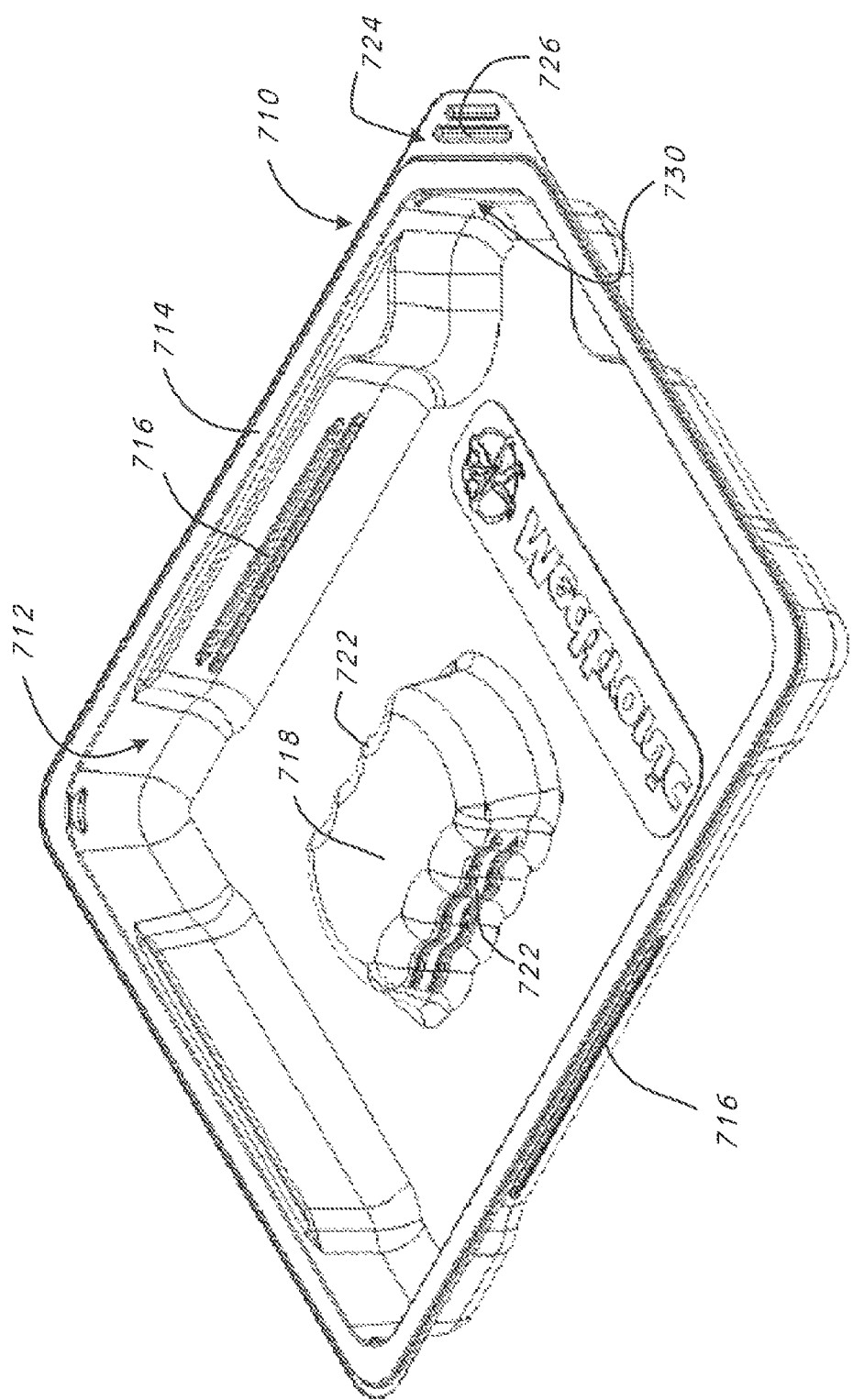
FIG. 28 is an isometric view of the blister shell shown in FIG. 27.

FIG. 28 illustrates the blister shell 710, which includes a surrounding sidewall 712 and a sealing flange 714. The sealing flange 714 provides a sealing surface against which the lidding sheet 715 can be sealed. In one embodiment, for example, the lidding sheet 715 may be comprised of a variety of suitable lidding materials (e.g., high density polyethylene (HDPE) or another suitable plastic material). In one embodiment, for example, the lidding sheet 715 may be comprised of Tyvek® material which is an HDPE lidding material available from DuPont™.

Surrounding sidewall 712 includes outwardly facing gripping features 716 to facilitate grasping the blister shell 710 for removal of lidding material 715. Grip tab 724 extends from the sealing flange 714 and includes gripping features 726. Blister shell 710 also includes a central boss 718 which helps locate the catheter container 720 in the blister shell 710. Central boss 718 also includes gripping features 722 to further facilitate grasping the blister shell 710 for removal of the lidding sheet 715. In one embodiment, the surrounding sidewall 712 includes a chamfered region 730 to help prevent the catheter container 720 from being inserted incorrectly.

Figure 29:
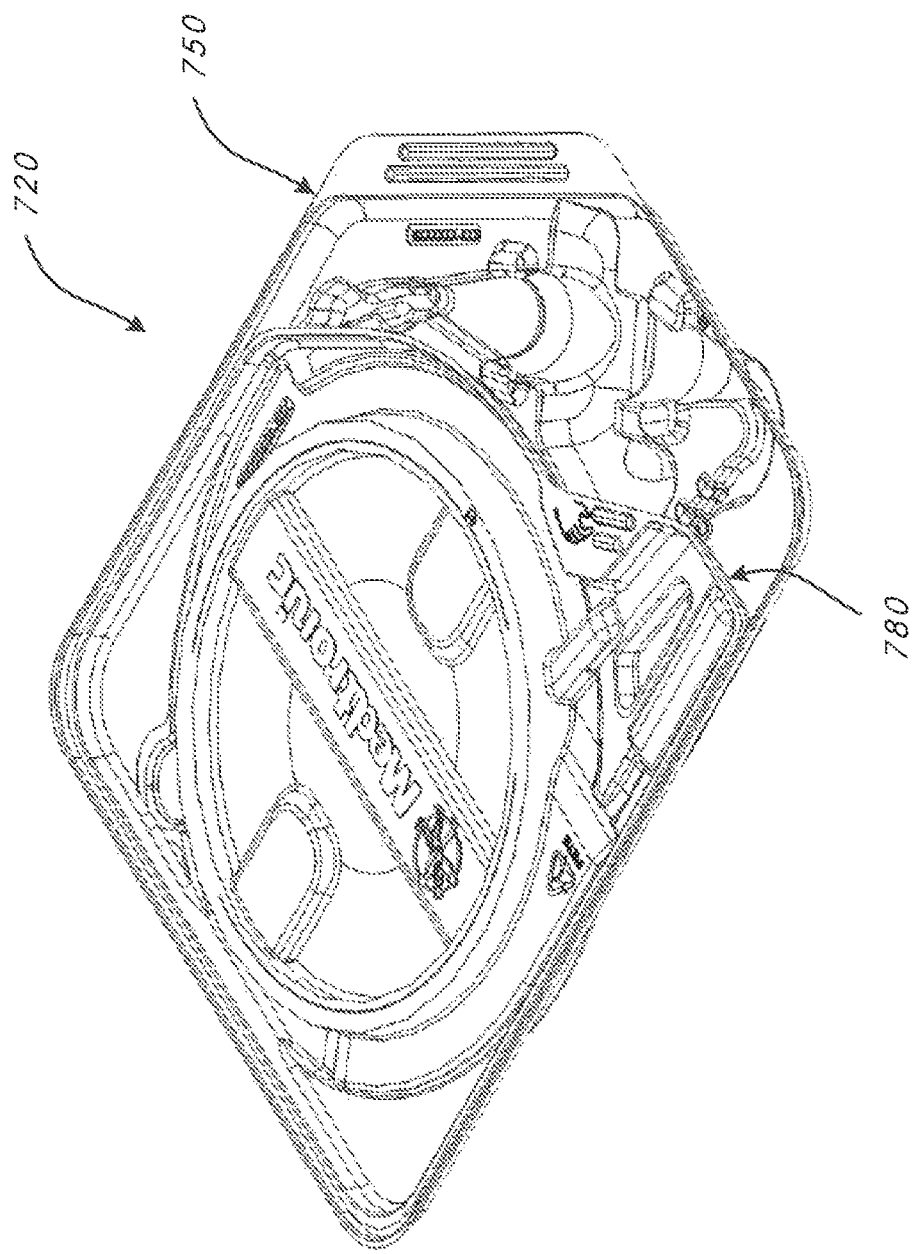
FIG. 29 is an isometric view of the catheter container shown in FIG. 27.

FIG. 29 illustrates the catheter container 720 including tray 750 and mating lid 780. Catheter container 720 includes similar features to those described above with respect to FIGS. 15-23. However, in this embodiment, the catheter container 720 includes features to facilitate bracing the catheter container 720 within the blister shell 710. For example, the catheter container 720 has a shape which is generally congruent with the shape of the surrounding sidewall 712 of the blister shell 710. In one embodiment, for example, the catheter container 720 and blister shell 710 are generally rectangular in shape.

Figure 30:
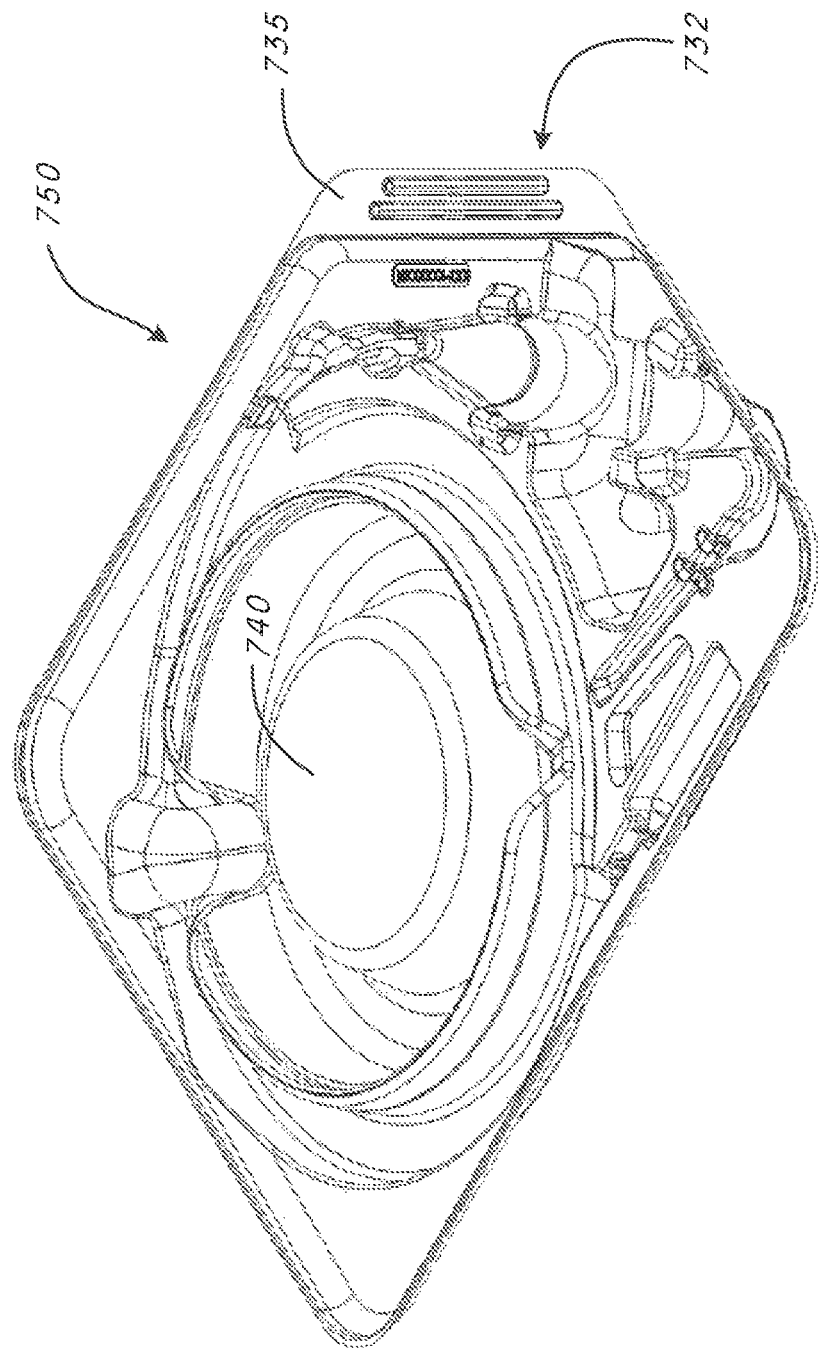
FIG. 30 is an isometric view of the tray shown in FIGS. 27 and 29.

FIG. 30 illustrates the tray 750 including an inner boss 740 to help maintain the catheter cable (see FIG. 12, for example) in position during distribution and handling of the catheter package assembly 705. The tray 750 includes a chamfered corner 732 which is alignable with the chamfered region 730 of the blister shell 710. The tray 750 also includes a grip tab 735 that may be used to remove the catheter container 720 from blister shell 710. In some embodiments, the grip tab 735 is spaced away from chamfered region 730 to provide access for grasping the grip tab 735. The grip tab 735 may also be used in conjunction with grip tab 737, as shown in FIG. 31, to separate the lid 780 from tray 750.

Figure 31:
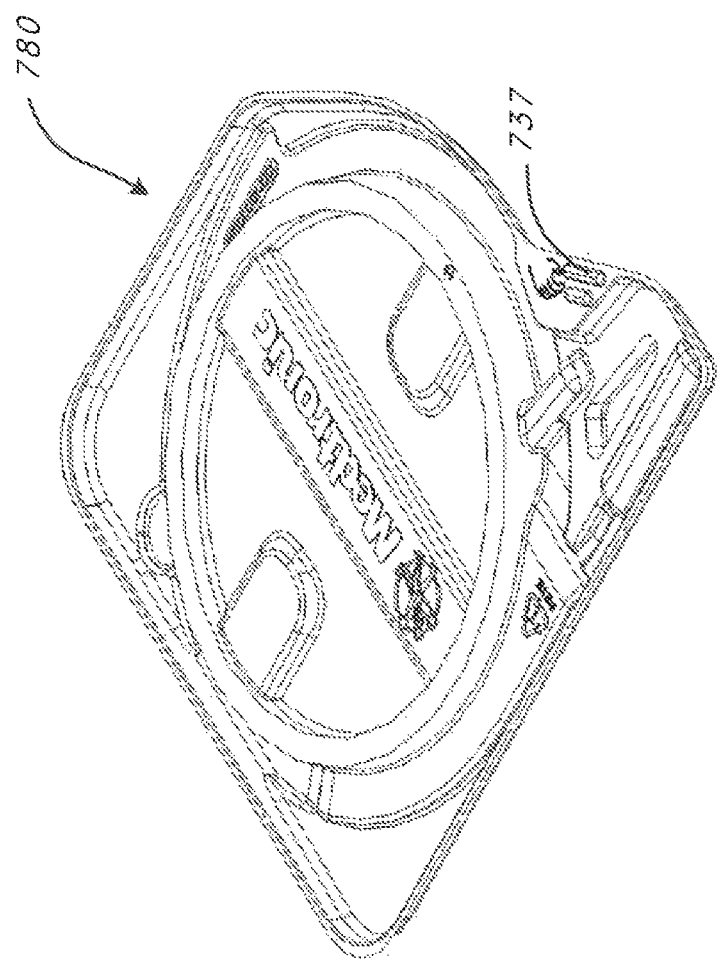
FIG. 31 is an isometric view of the lid shown in FIGS. 27 and 29.

FIG. 31 illustrates the lid 780, which includes features similar to those of lid 680 described above with respect to FIGS. 15 and 16. The lid 780 of the catheter container 720 is configured to mate with the tray 750 to provide an enclosed container.

IV. Protective Boxes

Figure 24A:
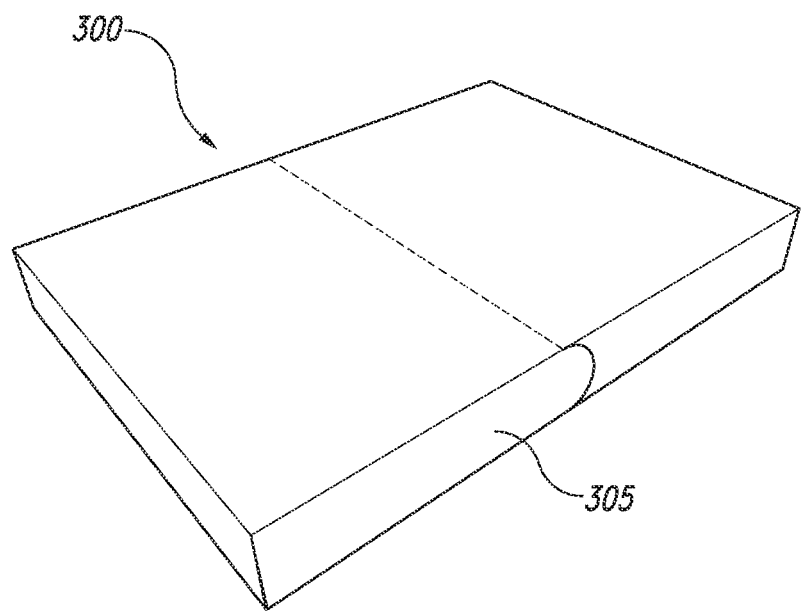
FIG. 24A is an isometric view of a box configured in accordance with an embodiment of the present technology for storing a catheter container.
Figure 24B:
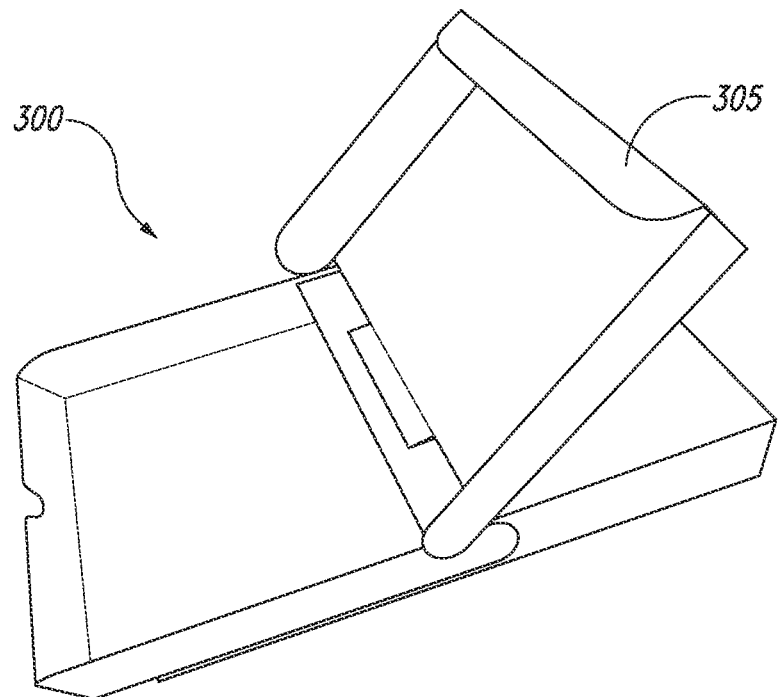
FIG. 24B is an isometric view of the box of FIG. 24A in an open configuration.

In some embodiments, the disclosed catheter package assemblies may also be packaged in a protective box. Conventional catheter boxes typically open at one end and require users to reach deep into the box to pull out the catheter. Such boxes also tend to use corrugate, which has an unclean stigma to it. FIGS. 24A and 24B, however, illustrate a protective box 300 configured in accordance with an embodiment of the present technology shown in a closed and an open configuration, respectively. The box 300 is configured to hold the catheter package as well as user instructions (e.g., a paper IFU) that may be required by some regulatory authorities. The box 300, for example, can be composed of solid bleached sulfate (SBS) and folded into the desired shape including a hinged lid 305. In other embodiments, the box 300 may be composed of different materials and/or have a different arrangement.

Figure 25A:
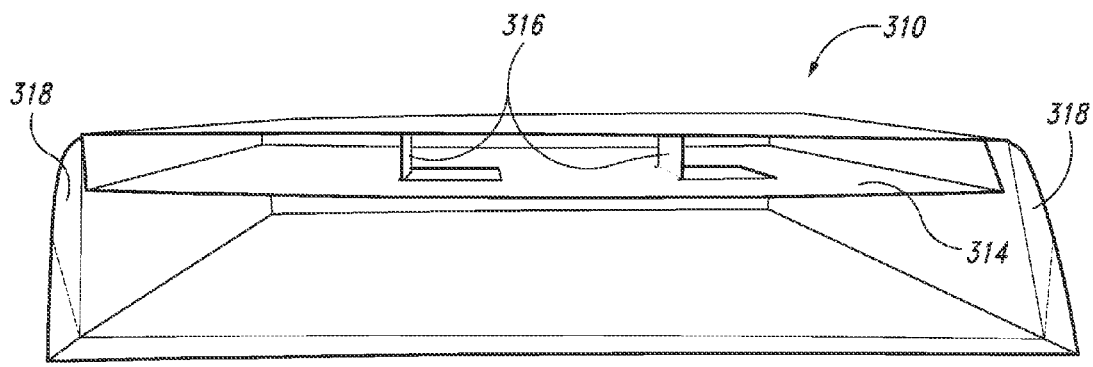
FIG. 25A is an end view of an alternative construction for the box shown in FIG. 24A.
Figure 25B:
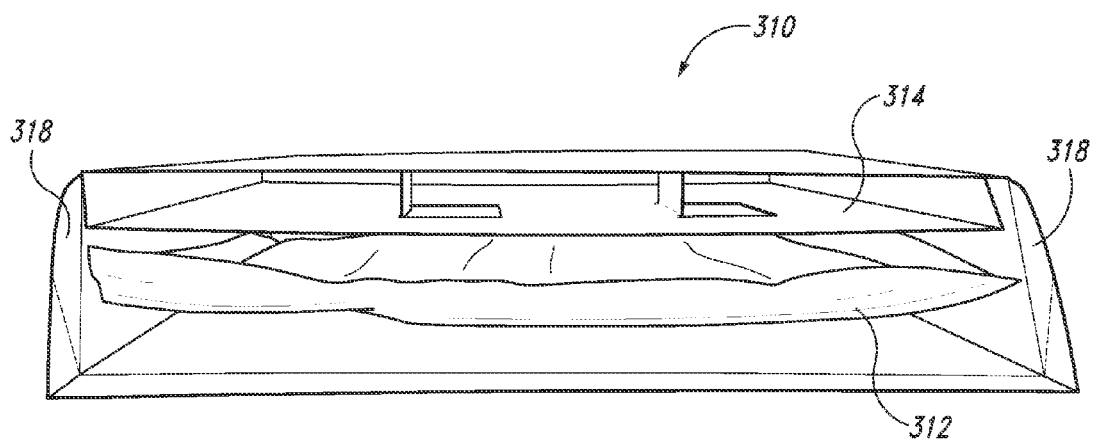
FIG. 25B is an end view of the box shown in FIG. 25A illustrating a catheter container in a sealed bag disposed in the box.

FIGS. 25A and 25B illustrate a protective box 310 configured in accordance with another embodiment of the present technology. As best seen in FIG. 25B, the catheter package assembly may be enclosed in a sterile bag 312 and inserted into the box 310 for shipping. Box 310 includes gussets 318 which are folded inward along perforation lines as the box is closed. Gussets 318 provide added structural support to protect the paperboard box design from corner crushing. The protective box 310 can include a pocket divider 314 to separate the IFU manual from the sterile barrier header bag 312, as well as to pin gussets 318 outward thus preventing contact between the gussets 318 and the sterile bag 312. The pocket divider 314 may be supported by a pair of stanchions 316.

As shown in the flat pattern of FIG. 26, the gussets 318 can be modified by creating an indentation bump 320 that helps minimize the sharpened point that would be created once folded. The gussets 318 are shown as an indentation 320 or bumped in. Alternatively, they could be formed with a bumped out arrangement. In still further embodiments, the box 310 may have a different arrangement and/or include different features.

V. Examples

The following examples are illustrative of several embodiments of the present technology:

1. A catheter package assembly for removably storing a catheter, the catheter package assembly comprising:
   a tray including at least one pocket adapted to receive a multi-electrode array at a distal portion of the catheter;
   a lid pivotably attached to the tray, wherein the tray and lid each include cooperative latching features;
   a sheath assembly disposed in the tray, wherein the sheath assembly defines a lumen therethrough configured to receive an elongate shaft of the catheter; and
   a plurality of clips removably attached to the sheath assembly and configured to retain the sheath assembly in a coiled configuration in the tray.

2. The catheter package assembly of example 1 wherein the tray further comprises a handle pocket configured to receive a handle of the catheter.

3. The catheter package assembly of example 1 or example 2 wherein the tray further comprises a plurality of protrusions positioned to engage the sheath assembly and removably retain the sheath assembly in the tray in a snap fit arrangement.

4. The catheter package assembly of any one of examples 1 to 3 wherein the lid, when cooperatively mated with the tray, is configured to cover only the sheath assembly and the multi-electrode array of the catheter.

5. A catheter package assembly for removably containing and protecting a catheter, the catheter container comprising:
   a tray including—
      a pocket configured to receive a therapeutic assembly at a distal portion of the catheter;
      a handle pocket configured to receive a handle of the catheter; and
      a channel extending between the pocket and handle pocket, wherein the channel includes a coil groove;
   a sheath removably disposed in the coil groove, wherein the sheath comprises a lumen therethrough configured to receive an elongate shaft of the catheter; and
   a lid configured to mate with the tray and provide an enclosed container for a portion of the catheter.

6. The catheter package assembly of example 5 wherein the tray includes a plurality of protrusions adjacent the handle pocket and positioned to removably retain the handle in the handle pocket.

7. The catheter package assembly of example 5 or example 6 wherein the lid comprises a lid pocket cover and a lid channel cover portion, and wherein, when the lid is mated with the tray in a closed configuration—
   the pocket cover and lid pocket cover cooperatively contain and protect the therapeutic assembly at the distal portion of the catheter; and
   the channel cover portion and lid channel cover portion cooperatively contain and protect the sheath.

8. The catheter package assembly of any one of examples 5 to 7, further comprising a cable assembly cavity in the coil groove.

9. The catheter package assembly of any one of examples 5 to 8 wherein the sheath is secured to itself, thereby retaining the sheath in a coiled configuration.

10. The catheter package assembly of any one of examples 5 to 9 wherein the coiled sheath is welded to itself.

11. The catheter package assembly of any one of examples 5 to 10 wherein the channel further comprises a retainer feature proximate the pocket, and wherein the retainer feature is configured to removably retain the sheath in the channel.

12. The catheter package assembly of example 11 wherein the channel comprises an end stop feature between the retainer feature and the pocket, and wherein the sheath assembly is configured to be retained in the channel against the end stop feature by the retainer feature.

13. A catheter package assembly, comprising:
   a tray including at least one pocket adapted to receive a therapeutic assembly at a distal portion of a catheter; and
   a coiled sheath removably disposed in the tray, wherein the sheath defines a lumen therethrough, and wherein the lumen is configured to receive an elongate shaft of the catheter.

14. The catheter package assembly of example 13 further comprising a lid pivotably coupled to the tray.

15. The catheter package assembly of example 14 wherein the tray and lid each include cooperative latching features.

16. The catheter package assembly of example 14 or example 15 wherein the lid includes a pocket cover.

17. The catheter package assembly of any one of examples 13 to 16 wherein the tray includes a handle pocket.

18. The catheter package assembly of any one of examples 13 to 17, further comprising a plurality of clips attached to the sheath and positioned to retain the sheath in a coiled configuration.

19. The catheter package assembly of any one of examples 13 to 18 wherein the tray includes a plurality of protrusions positioned to retain the coiled sheath in the tray.

20. The catheter package assembly of any one of examples 13 to 17 wherein the tray includes protrusions configured to grasp the sheath and retain the sheath in a coiled configuration.

21. The catheter package assembly of any one of examples 1 to 20 further comprising a blister shell configured to receive the tray.

22. The catheter package assembly of example 21 further comprising a lidding sheet attached to a sealing flange of the blister shell.

VI. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, the catheter package assemblies and catheter containers described herein may be used with catheters having therapeutic assemblies with a variety of different configurations (e.g., single electrode, expandable basket, expandable balloon, one or more transducers, etc.). Further, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A catheter package assembly for removably containing and protecting a catheter, the catheter package assembly comprising:
    a catheter container having a tray including—
        a therapeutic assembly pocket configured to receive a therapeutic assembly at a distal portion of the catheter;
        a handle pocket configured to receive a handle of the catheter;
        a wire path extending from the handle pocket an including a plurality of nubs positioned to grasp a cable assembly of the handle; and
        a channel extending between the therapeutic assembly pocket and the handle pocket, wherein the channel includes a coil groove;
    a sheath removably disposed in the coil groove, wherein the sheath comprises a lumen therethrough configured to receive an elongate shaft of the catheter; and
    a lid configured to mate with the tray and provide an enclosed container for a portion of the catheter;
    a blister shell including a surrounding sidewall and a sealing flange, wherein the shape of the surrounding sidewall is congruent with the shape of the catheter container; and
    a lidding sheet configured to mate to the sealing flange and provide an enclosed container.

2. The catheter package assembly of claim 1 wherein the tray further comprises a plurality of protrusions positioned to engage the sheath and removably retain the sheath in the tray in a snap fit arrangement.

3. The catheter package assembly of claim 1 wherein the tray includes a plurality of protrusions adjacent the handle pocket and positioned to removably retain the handle in the handle pocket.

4. The catheter package assembly of claim 1 wherein the lid comprises a lid pocket cover and a lid channel cover portion, and wherein, when the lid is mated with the tray in a closed configuration—
    the therapeutic assembly pocket and the lid pocket cover cooperatively contain and protect the therapeutic assembly at the distal portion of the catheter; and
    the channel and the lid channel cover portion cooperatively contain and protect the sheath.

5. The catheter package assembly of claim 1 wherein the coiled sheath is secured to itself, thereby retaining the sheath in a coiled configuration.

6. The catheter package assembly of claim 5 wherein the coiled sheath is welded to itself.

7. The catheter package assembly of claim 1 wherein the channel further comprises a retainer feature proximate the therapeutic assembly pocket, and wherein the retainer feature is configured to removably retain the sheath in the channel.

8. The catheter package assembly of claim 7 wherein the channel comprises an end stop feature between the retainer feature and the therapeutic assembly pocket, and wherein the sheath assembly is configured to be retained in the channel against the end stop feature by the retainer feature.

9. The catheter package assembly of claim 1, further comprising a boss protruding centrally in the blister shell to help locate the catheter container therein.

10. The catheter package assembly of claim 1, further comprising an inner boss protruding centrally in the cable assembly cavity to help position a cable of the catheter therein.

* * * * *